(12) United States Patent
Monassevitch et al.

(10) Patent No.: US 6,896,684 B2
(45) Date of Patent: May 24, 2005

(54) SURGICAL CLIP APPLICATOR DEVICE

(75) Inventors: Leonid Monassevitch, Givat Olga (IL); Shlomo Lelcuk, Savion (IL); Michael Arad, Tel-Aviv (IL); Boaz Harari, Savion (IL); Ronen Neeman, Haifa (IL)

(73) Assignee: NiTi Medical Technologies Ltd., Netanya (IL)

( * ) Notice: Subject to any disclaimer, the term of this patent is extended or adjusted under 35 U.S.C. 154(b) by 0 days.

(21) Appl. No.: 10/158,673

(22) Filed: May 30, 2002

(65) Prior Publication Data

US 2002/0177859 A1 Nov. 28, 2002

Related U.S. Application Data

(63) Continuation-in-part of application No. 09/592,518, filed on Jun. 12, 2000, now Pat. No. 6,402,765.

(51) Int. Cl.$^7$ .......................... A61B 17/10; A61B 17/08; A61B 17/28
(52) U.S. Cl. .................. 606/142; 606/151; 606/207
(58) Field of Search .................. 606/139, 142, 606/144, 151–158, 174, 207, 208, 210, 120

(56) References Cited

U.S. PATENT DOCUMENTS

| | | | | |
|---|---|---|---|---|
| 3,735,762 A | * | 5/1973 | Bryan et al. | 606/143 |
| 4,152,920 A | * | 5/1979 | Green | 72/409.05 |
| 4,412,539 A | * | 11/1983 | Jarvik | 606/143 |
| 4,576,165 A | * | 3/1986 | Green et al. | 606/143 |
| 5,171,252 A | | 12/1992 | Friedland | |
| 5,176,544 A | | 1/1993 | AbuJudom, II et al. | |
| 5,591,173 A | * | 1/1997 | Schifano | 606/120 |
| RE36,720 E | * | 5/2000 | Green et al. | 606/151 |
| 6,088,889 A | | 7/2000 | Luther et al. | |
| 6,171,320 B1 | | 1/2001 | Monassevitch | |
| 6,206,913 B1 | | 3/2001 | Yencho et al. | |
| 6,254,615 B1 | | 7/2001 | Bolduc et al. | |
| 6,517,556 B1 | * | 2/2003 | Monassevitch | 606/151 |

FOREIGN PATENT DOCUMENTS

| | | |
|---|---|---|
| EP | 0 326 757 | 7/1993 |
| SU | 1186199 | 10/1985 |

\* cited by examiner

Primary Examiner—Glenn K. Dawson
Assistant Examiner—D. Jacob Davis
(74) Attorney, Agent, or Firm—Pearne & Gordon LLP

(57) ABSTRACT

The present invention, discloses an anastomosis clip applicator device for applying a surgical clip, formed at least partly of a shape memory alloy, to press together adjacent wall portions of adjacent hollow organ portions so as to effect anastomosis therebetween. The applicator device includes: gripping apparatus for gripping a surgical clip, a release mechanism, associated with the gripping apparatus, and tissue cutting apparatus, operatively associated with the gripping apparatus. There is also apparatus for activating the gripping apparatus, the release mechanism and the cutting apparatus, so as to introduce and apply the surgical clip into adjacent hollow organ portions, such that the surgical clip compresses together the adjacent walls of the hollow organ portions, and thereafter causes the cutting apparatus to perforate the adjacent pressed together organ walls to provide patency through the joined portions of the hollow organ.

13 Claims, 24 Drawing Sheets

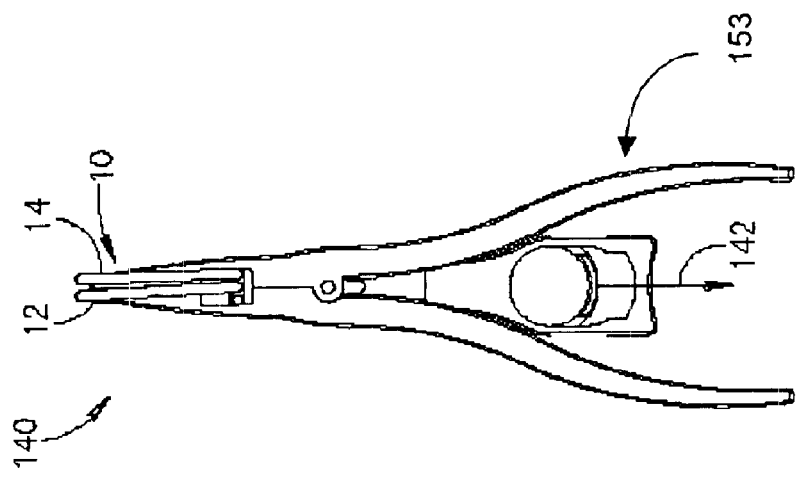
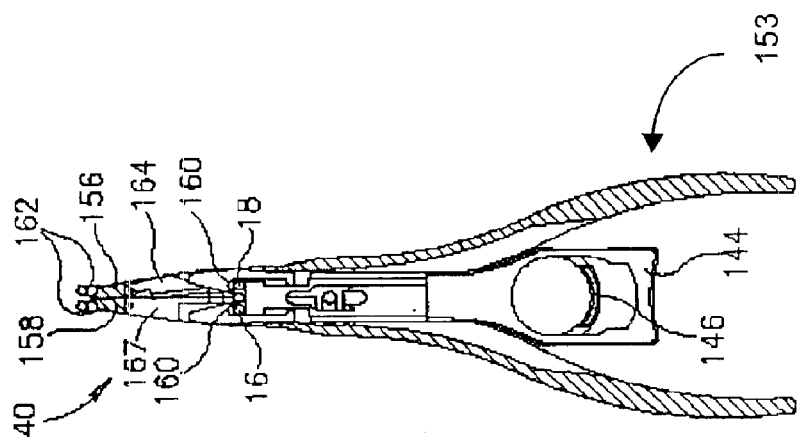
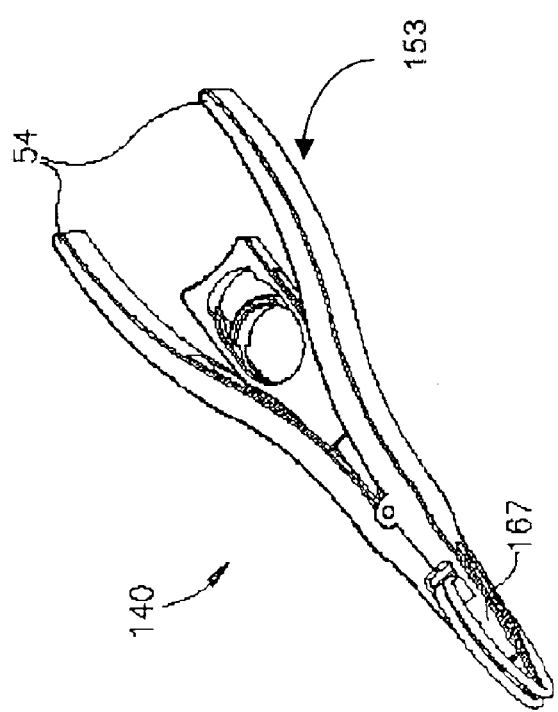

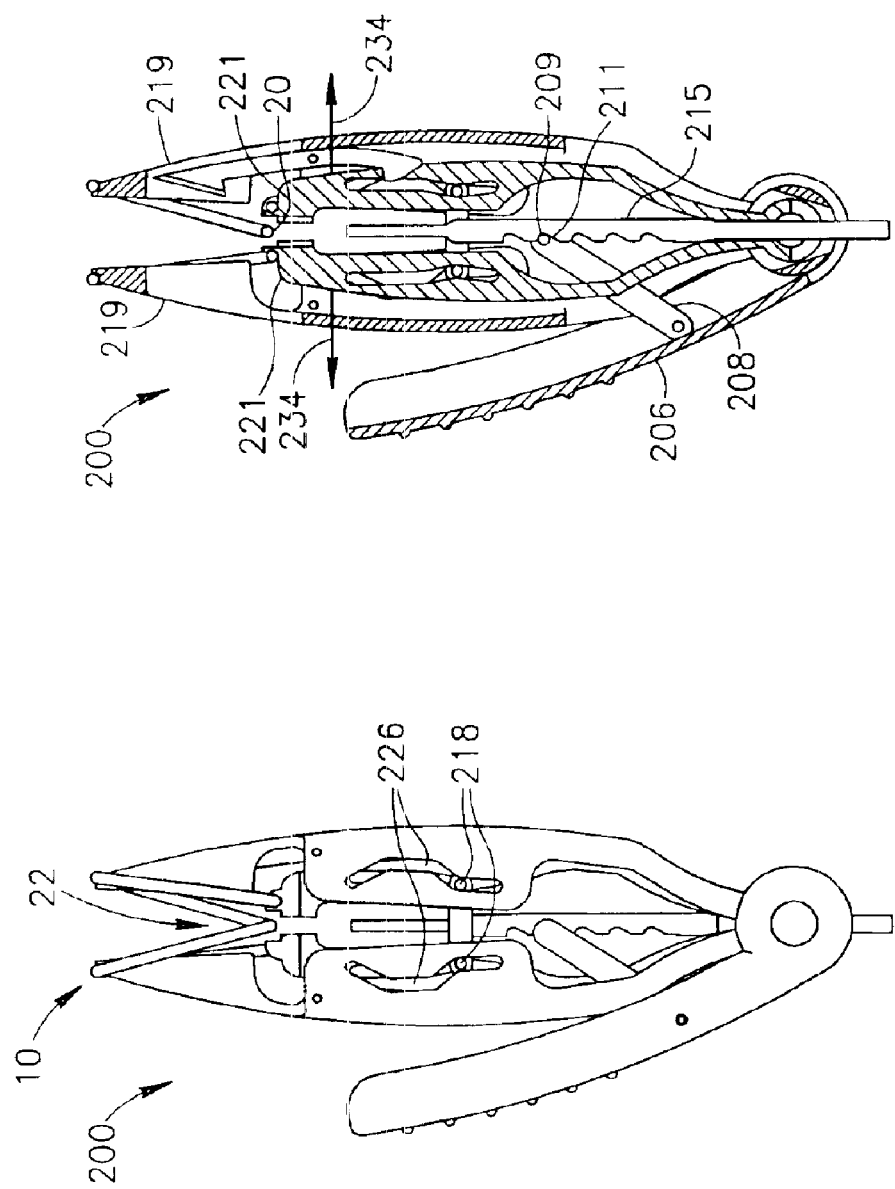

SURGICAL CLIP APPLICATOR DEVICE

REFERENCE TO CO-PENDING APPLICATIONS

The present application is a continuation-in-part of U.S. application Ser. No. 09/592,518 filed on Jun. 12, 2000 for "SURGICAL CLIP", now U.S. Pat. No. 6,402,765, the contents of which are incorporated herein, by reference.

FIELD OF THE INVENTION

The present invention relates to the field of surgical clips, in general, and in particular, to the field of surgical clip applicator devices.

GLOSSARY

ANASTOMOSIS: The union of parts or branches (as of hollow organs or blood vessels) so as to intercommunicate therebetween.

BACKGROUND OF THE INVENTION

It is known in the art to provide methods for joining portions of hollow organs, such as the gastrointestinal tract. These include threads for manual suturing, staplers for mechanical suturing, and compression rings and clips.

While manual suturing is universally known and relatively inexpensive, the degree of success depends considerably on the skill of the surgeon. Another disadvantage is that post-operative complications are common. Further, suturing an organ results in lack of smoothness of the tissue therein, which, when the sutured organ is part of the gastrointestinal tract, hampers peristalsis in the sutured area. Finally, suturing is both labor and time consuming.

Staplers for mechanical suturing ensure a reliable joining of tissue and enable the time needed for surgery to be reduced, compared with manual suturing. However, due to the facts that such staples are not reusable and that a great many types and sizes are required, the price of staples is high. Also, after healing, metal staples remain in place along the perimeter of the suture, which reduces elasticity of the junction and adversely affects peristalsis when the sutured organ is part of the gastrointestinal tract.

Junctions using compression devices such as rings and clips ensure the best seal and post-operative functioning of the organs. Two types of compression devices are known, namely, rings made of resorption plastics and clips made of memory alloys. Plastic rings are cumbersome and expensive. Also, the compression force is applied only momentarily at the junction and is reduced as the tissue is crushed. Clips made of shape memory alloys enable portions of tissue to be pressed together when equilibrium with body temperature is reached, whereat, due to the inherent properties of the alloys, the clips resume their memorized shape.

Development of clips made of memory alloy materials has increased recently, as they have many advantages over other devices. Their design is simple, they are cheap, they are small in size and possess universal qualities, and they are self-evacuated from the gastrointestinal tract.

It is known in the art to provide a surgical fastening clip which applies a clamping force to a site, such as a blood vessel, thereby reducing its cross-sectional area. It is also known to provide a surgical fastening clip formed of a shape memory alloy which deforms to a closed configuration when heated, such that the clamping force applied thereby is increased as it is heated. For example, U.S. Pat. No. 5,171,252 discloses a surgical fastening clip formed of a shape memory alloy; the device disclosed therein includes separate legs which close tightly around a site. Such a device is limited in its uses, such as for clamping blood vessels, and is not suitable for joining portions of the gastrointestinal tract.

EP 0,326,757 discloses a device for anastomosing a digestive tract, which includes a plurality of U-shaped retaining clips disposed around a soluble support tube. The tube is positioned inside portions of the digestive tract to be joined, and includes an outer groove around which are disposed the U-shaped retaining clips. The retaining clips are made of a shape memory alloy such that the open ends thereof close at a predetermined temperature, thus joining ends of the digestive tract. Once the ends of the digestive tract have been joined, the tube is dissolved. Such a device is disadvantageous in that its use requires a plurality of clips to be properly positioned simultaneously. Also, there is no assurance that the resulting junction will be smooth, due to the plurality of sites of the digestive tract joined by the plurality of clips.

SU 1,186,199 discloses a memory alloy clip consisting of two parallel coils to be used for joining portions of a hollow organ, such as an organ of the gastrointestinal tract. The portions of the organ to be joined are aligned, and each of the plastic coils is introduced through a puncture formed in the wall of one of the portions. The coils are positioned such that, when heated, they compress the aligned walls therebetween, thus maintaining the portions of the walls held within the loops of the coils adjacent each other. Thereafter, incisions are made through the portions of the walls held within the loops of the coils, such that a passageway is created between the two organ portions. The punctures in the organ walls must then be surgically sewn closed with interrupted surgical sutures.

A major disadvantage of known memory alloy clips is that they permit compression of only approximately 80–85% of the junction perimeter, thus requiring additional manual sutures, which reduce the seal of the junction during the healing period and its elasticity during the post-operative period. Also, this additional suturing is problematic inasmuch as it has to be carried out across a joint which includes a portion of the clip, thereby rendering difficult the sealing and anastomosis of the organ portions. Furthermore, once in place, clips according to the prior art require further surgery to be performed, namely, incisions through tissue so as to create a passageway between the two organ portions which have been joined by the clip.

There is thus a need for a surgical device which facilitates compression of substantially the entire perimeter of the junction between the organ portions being joined, which would obviate the need for additional manual sutures and which ensures the smooth seal of the junction during the healing period and its elasticity during the post-operative period. Additionally, there is a need for a surgical device which, once in place, would enable a passageway to be created between the two organ portions which have been joined together, without requiring further surgery to be performed on the organ.

SUMMARY OF THE INVENTION

In seeking to achieve the above objectives, and in accordance with a preferred embodiment of the present invention, suitable apparatus, for example, is described in the Applicant's co-pending U.S. application Ser. No. 09/592,518, for "SURGICAL CLIP".

In order to achieve anastomosis of two portions of a hollow organ or of two hollow organs, the present invention seeks to provide a surgical clip for joining these and for providing a seal while anastomosis occurs. Furthermore, the present invention seeks to provide a device for applying the surgical clip to the organs to be joined to facilitate the anastomosis surgical procedure.

According to a preferred embodiment of the present invention, there is provided an anastomosis clip applicator device for applying a surgical clip to press together adjacent wall portions of adjacent hollow organ portions so as to effect anastomosis between the adjacent organ portions. The applicator device includes:

gripping apparatus for gripping a surgical clip, configured to permit positioning of the clip into a pair of adjacent hollow organ portions;

a release mechanism, associated with the gripping apparatus, for selectably releasing the clip from the gripping apparatus when the clip is positioned in a selected position about a pair of organ walls to be anastomosed;

tissue cutting apparatus, operatively associated with the gripping apparatus, selectably operable, after positioning of the clip, to cut through the tissue walls so as to form therethrough a predetermined perforation; and apparatus for activating the gripping apparatus, the release mechanism and the cutting apparatus, so as to introduce and apply the surgical clip into adjacent hollow organ portions, such that the surgical clip compresses together the adjacent walls of the hollow organ portions, and thereafter causes the cutting apparatus to perforate the adjacent pressed together organ walls.

Also, in accordance with a preferred embodiment of the present invention, the anastomosis clip applicator device cutting apparatus includes a blade element and a counter element, wherein the blade and counter elements are arranged in mutually opposing registration, and adapted to be closable in mutual mating engagement, thereby to perforate tissue located therebetween.

Additionally, in accordance with preferred embodiments of the present invention, the anastomosis clip applicator device is formed having a configuration that is tong-like, plier-like, scissors-like, forceps-like or of other suitable configurations. Further, the anastomosis clip applicator device includes ejector apparatus for disengaging and ejecting the clip from the gripping apparatus. Also, the clip applicator device gripping apparatus includes one or more pairs of fastener elements for securing the clip to the applicator device.

Likewise, in accordance with a preferred embodiment of the present invention, the anastomosis clip applicator device counter element is a second blade element.

In addition, in accordance with a preferred embodiment of the present invention, the anastomosis clip applicator device has a proximal end portion and a distal end portion. The gripping apparatus, the one or more blade elements and the one or more counter elements are formed at the distal end and the distal end portion is detachable from the proximal end portion.

Furthermore, there is provided a method for anastomosing a gastrointestinal tract, which includes the following steps:

gripping a surgical clip,
wherein the surgical clip includes a first length of a wire defining a closed geometrical shape having a central opening, a second length of a wire defining a closed geometrical shape substantially similar in configuration and magnitude to that of the first length of wire, having a central opening, wherein the first and second lengths of wire fully overlap, when configured in side-by-side registration, and an intermediate portion located between the first length of wire and the second length of wire, the intermediate portion formed of a shape memory alloy;

maintaining at least the intermediate portion of the clip at a temperature below a lower phase transition temperature thereof, whereat the intermediate portion is in a plastic state;

moving the first and second lengths of wire into a position of mutual separation;

drawing together portions of the gastrointestinal tract, wherein anastomosis is required, so as to bring them into an adjacent, side-by-side position, one or both of the portions being open-ended;

surgically sealing the open ends of the portions of the gastrointestinal tract;

forming predetermined perforations in adjacent walls of the adjacent portions of gastrointestinal tract and introducing the clip through the punctures, such that the adjacent portions of each wall are disposed between the first and second lengths of wire; and retaining the relative adjacent positions of the portions of the gastrointestinal tract and the clip in relation thereto, while raising the temperature of at least the intermediate portion of the clip to a temperature above an upper phase transition temperature, whereat the intermediate portion is in an elastic state, thereby causing the first and second lengths of wire to attain side-by-side registration, thereby to apply a compressive force to the walls located therebetween.

According to an embodiment of the present invention, the method includes, subsequent to the step of retaining, an additional step of perforating the adjacent walls, held within the central openings between the first and second lengths of wire configured in side-by-side registration for creating an initial patency of the gastrointestinal tract.

Also, in accordance with a preferred embodiment of the present invention, there is provided an anastomosis system for applying one or more surgical clips formed at least partly of a shape memory alloy which includes, one or more surgical clips, each including:
a first length of a wire defining a closed geometrical shape having a central opening;

a second length of a wire defining a closed geometrical shape substantially similar in configuration and magnitude to that of the first length of wire, wherein the first and second lengths of wire fully overlap, when disposed in side-by-side registration; and an intermediate portion located between the first length of wire and the second length of wire, the intermediate portion formed of a shape memory alloy, wherein, when at a first temperature or higher, the first and second lengths of wire are positioned in a side-by-side closed position and the shape memory alloy is in an elastic state, and further, when at a second temperature or lower, below the first temperature, the shape memory alloy is in a plastic state, thereby enabling the first and second lengths of wire to be moved into and to retain a spaced apart position, and upon heating of the clip to a temperature at least equal to the first temperature, the first and second lengths of wire return to the side-by-side closed position, thereby to apply a compressive force to tissue located therebetween; and an anastomosis clip applicator device for applying a surgical clip to press together adjacent wall portions of adjacent hollow organ portions so as to effect anastomosis between the adjacent organ portions, wherein the applicator device includes:

gripping apparatus for gripping a surgical clip, configured to permit positioning of the clip into a pair of adjacent hollow organ portions;

a release mechanism, associated with the gripping apparatus, for selectably releasing the clip from the gripping apparatus when the clip is positioned in a selected position about a pair of organ walls to be anastomosed;

tissue cutting apparatus, operatively associated with the gripping apparatus, selectably operable, after positioning of the clip, to cut through the tissue walls so as to form therethrough a predetermined perforation; and apparatus for activating the gripping apparatus, the release mechanism and the cutting apparatus, so as to introduce and apply the surgical clip into adjacent hollow organ portions, such that the surgical clip compresses together the adjacent walls of the hollow organ portions, and thereafter causes the cutting apparatus to perforate the adjacent pressed together organ walls.

Additionally, in accordance with a preferred embodiment of the present invention, the cutting apparatus includes a blade element and a counter element, wherein the blade and counter elements are arranged in mutually opposing registration, and adapted to be closable in mutual mating engagement, thereby to perforate tissue located therebetween.

Further, in accordance with preferred embodiments of the present invention, the geometrical shape of the clip is substantially a shape selected from circular, elliptical and other suitable shapes. In regard to the clip, the first length of wire and the second length of wire are defined by a continuous coil. The first length of wire and the second length of wire are two distinct lengths of wire, each defining a closed geometrical shape. Furthermore, the first length of wire and the second length of wire are formed having cross-sectional shapes that are substantially circular. Other cross-sectional shapes are circular, having planar surfaces formed therein such that, when configured in side-by-side registration, the planar surfaces of the first and second lengths of wire fully overlap, or elliptical, or other suitable shapes, thereby to control pressure applied to tissue compressed between the first and second lengths of wire.

Also, in accordance with a preferred embodiment of the present invention, one or more overlapping surfaces of the first length of wire and the second length of wire is formed having a surface configuration, which includes a plurality of parallel surface grooves, knurled, a plurality of spikes, a plurality of studs or other surface configurations.

Additionally, in accordance with a preferred embodiment of the present invention, the gripping apparatus includes one or more pairs of fastener elements for securing the clip to the applicator device.

Further in accordance with preferred embodiments of the present invention, the system includes the counter element formed as a second blade element. Also, the applicator device includes ejector apparatus for disengaging and ejecting the clip from the gripping apparatus.

In addition, in accordance with another embodiment of the system of the present invention, the applicator device has a proximal end portion and a distal end portion, wherein the gripping apparatus, the blade element and the one or more counter elements are formed at the distal end. Furthermore, the distal end portion is detachable from the proximal end portion.

BRIEF DESCRIPTION OF THE DRAWINGS

The present invention will be more fully understood and its features and advantages will become apparent to those skilled in the art by reference to the ensuing description, by way of non-limiting example only, taken in conjunction with the accompanying drawings, in which:

FIGS. 9A–14C illustrate an operative sequence of a pliers-type applicator device, having a surgical clip operatively attached thereto, including perspective, partial cross-sectional and full views;

FIGS. 15A–19B illustrate an operative sequence of a manually-sequential surgical clip applicator device, including perspective, partial cross-sectional and full views thereof, having a surgical clip operatively attached thereto, for open surgery and semi-laproscopic anastomosis;

DETAILED DESCRIPTION OF THE INVENTION

The present invention seeks to provide a surgical clip, substantially as described in the Applicant's co-pending U.S. application Ser. No. 09/592,518 for "SURGICAL CLIP." The clip is at least partially formed of a shape memory alloy, such as is known in the art, and which provides organ tissue compression along the entire periphery of the clip, thereby to ensure satisfactory joining or anastomosis of portions of an organ. The present invention further seeks to provide apparatus for positioning and applying the clip and, also, for perforating tissue portions held within the applied clip, whereby initial patency of the gastrointestinal tract is created. In addition, the present invention provides a method and system for performing anastomosis of organ portions, such as those of the gastrointestinal tract. The method employs the clip as well as apparatus for positioning and applying the clip and, also, for perforating a portion of tissue held within the clip, whereby initial patency of the gastrointestinal tract is created.

Figure 1A:
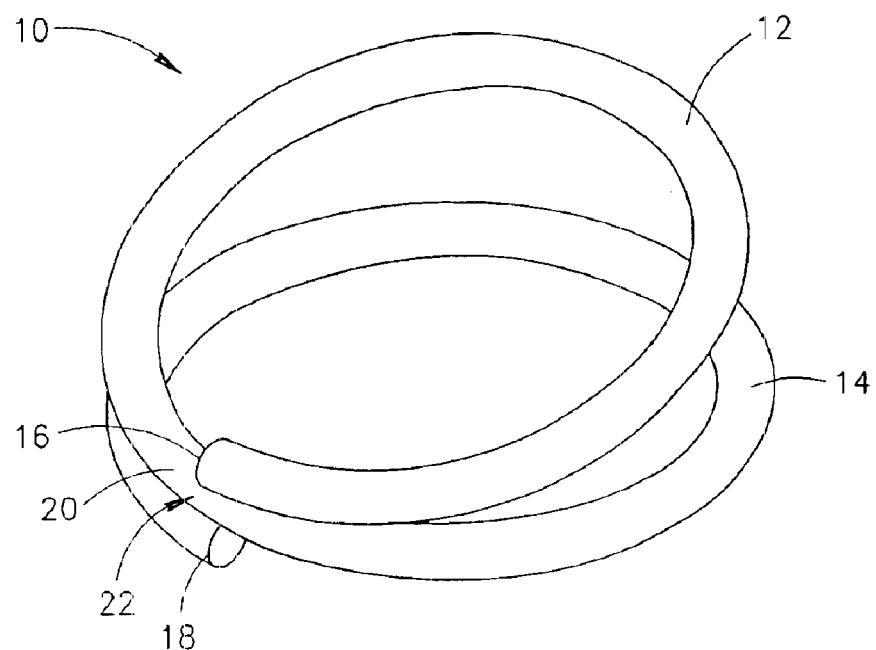
FIGS. 1A and 1B illustrate perspective views of a surgical clip, in an open, and in a closed configuration, respectively, according to an embodiment of the present invention.
Figure 1B:
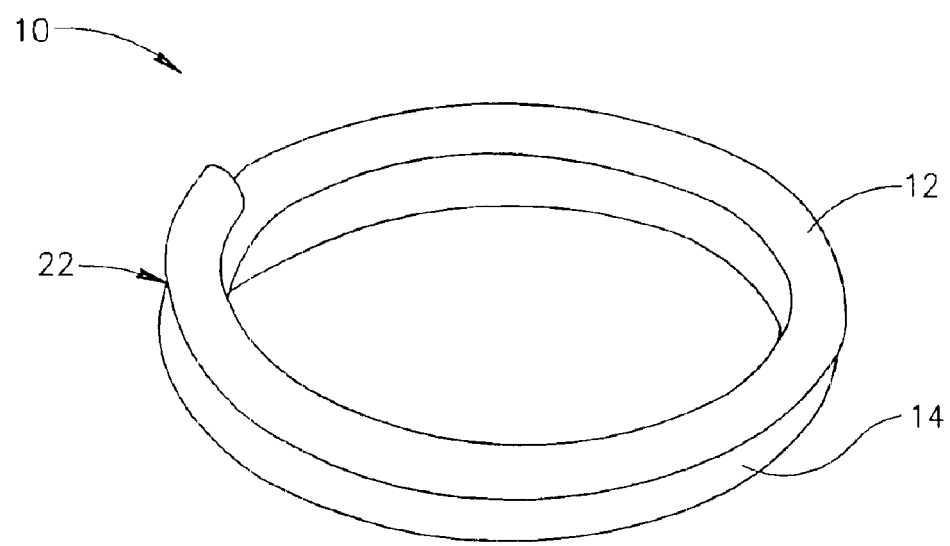

Referring now to FIGS. 1A and 1B there is seen a surgical clip, generally referenced 10, illustrated respectively in open and closed configurations. Clip 10 is typically wire-like, formed at least partly of a shape memory alloy, and is of a coiled configuration so as to include a pair of loops referenced 12 and 14, having respective ends referenced 16 and 18. Each of loops 12 and 14 defines a complete circle from its end to a point referenced 20 midway along the coil. Thus, clip 10 defines two complete circles from end 16 of loop 12 to end 18 of loop 14. While the various embodiments of the clip of the present invention are illustrated as defining circular shapes, it will be appreciated by persons skilled in the art that the present invention may, alternatively, define any closed geometric shape, such as an ellipse.

At least an intermediate portion generally referenced 22 of clip 10 is formed of a shape memory alloy such that, when cooled to below a predetermined temperature, the clip is in a plastic state, such that loops 12 and 14 may be moved apart, as seen in FIG. 1A. When heated to above the predetermined temperature, clip 10 changes to an elastic state, such that the loops 12 and 14 become adjacent to each other, as seen in FIG. 1B. While, if desired, the entire clip 10 may be formed of a shape memory alloy, it is essential that at least the intermediate portion 22 is formed of a shape memory alloy. The change in temperature, as it affects the shape memory alloy, will be discussed further hereinbelow, with reference to FIGS. 22A–22D.

While the surgical clip 10, is described in detail, hereinabove, in accordance with alternative embodiments of the present invention, surgical clips may be formed having other configurations, where surgically appropriate, in accordance with the organ size, position and other factors.

Figure 2A:
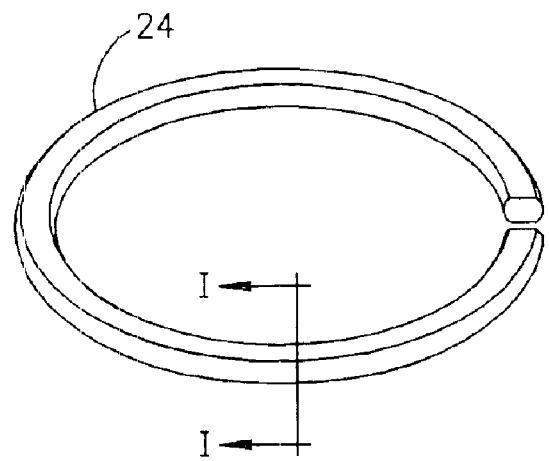
FIGS. 2A–2D illustrate partial-perspective and cross-sectional views of surgical clips having alternative cross-sectional profiles according to alternative embodiments of the present invention.
Figure 2B:
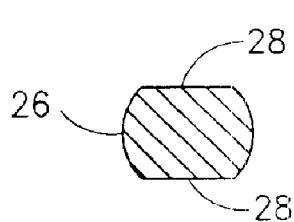
Figure 2C:
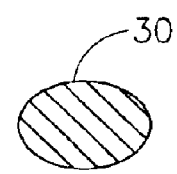
Figure 2D:
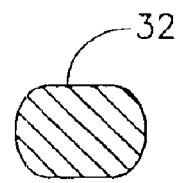

In order to control the pressure on the tissue walls at the point of contact with the clip, the cross-section of the wire forming the clip may be varied. Referring now to FIGS. 2A–2D, there is seen a partial-perspective view (FIG. 2A) of a surgical clip generally referenced 24 and cross-sectional views of alternative profiles taken along line I—I of surgical clip 24. In FIG. 2B there is seen a generally circular cross-sectional profile referenced 26, having planar surfaces referenced 28 formed therein according to an alternative embodiment of the present invention. In FIG. 2C there is seen an elliptical profile referenced 30, and in FIG. 2D an elliptical-type profile referenced 32.

Figure 3A:
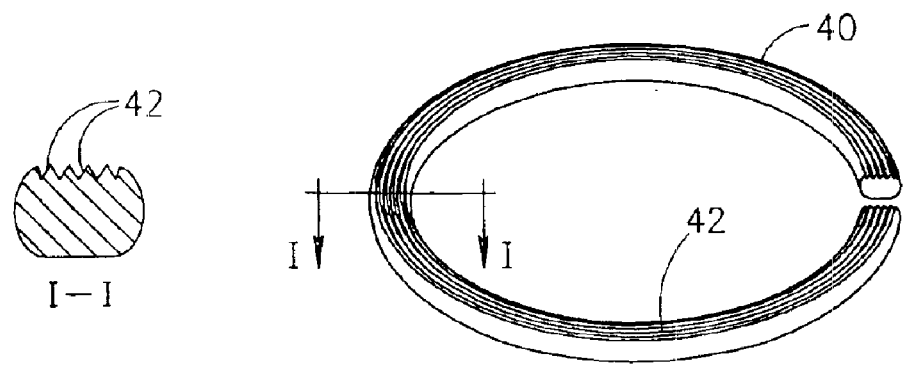
FIGS. 3A–3C illustrate partial-perspective and cross-sectional views of surgical clips having alternative gripping surfaces thereon according to an alternative embodiment of the present invention.
Figure 3B:
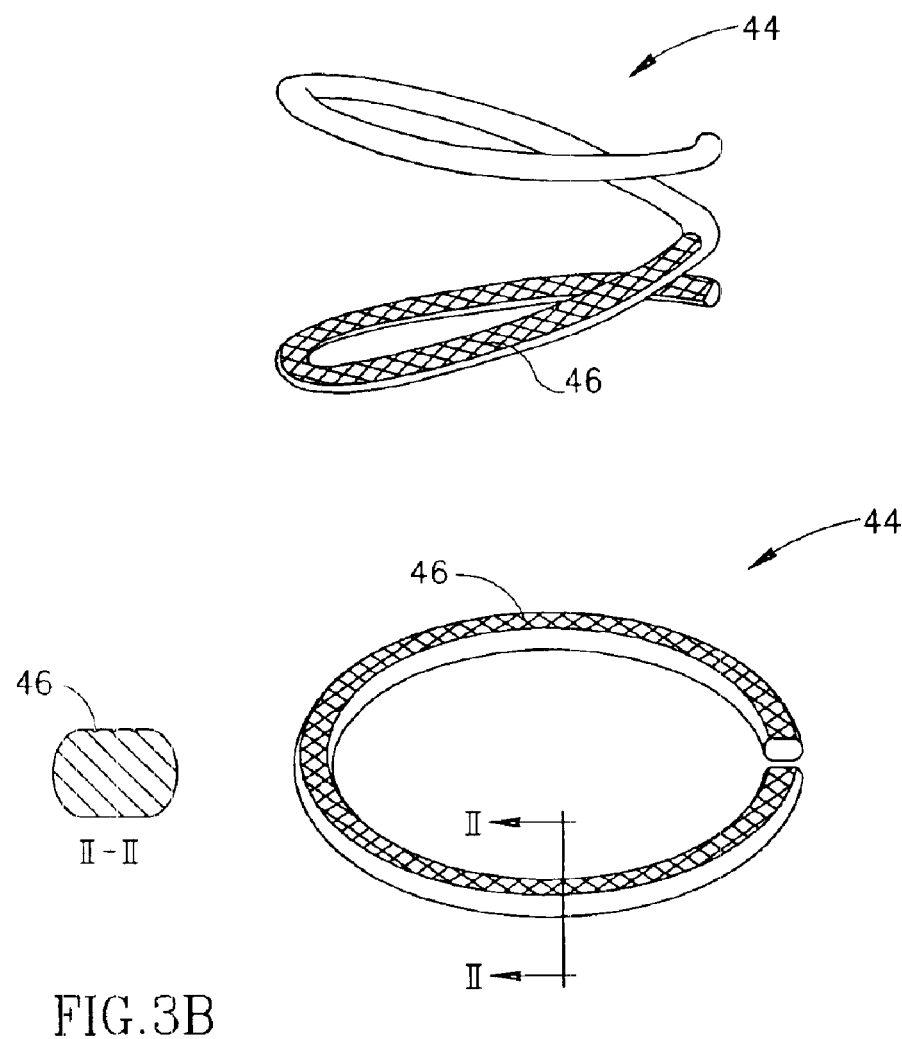
Figure 3C:
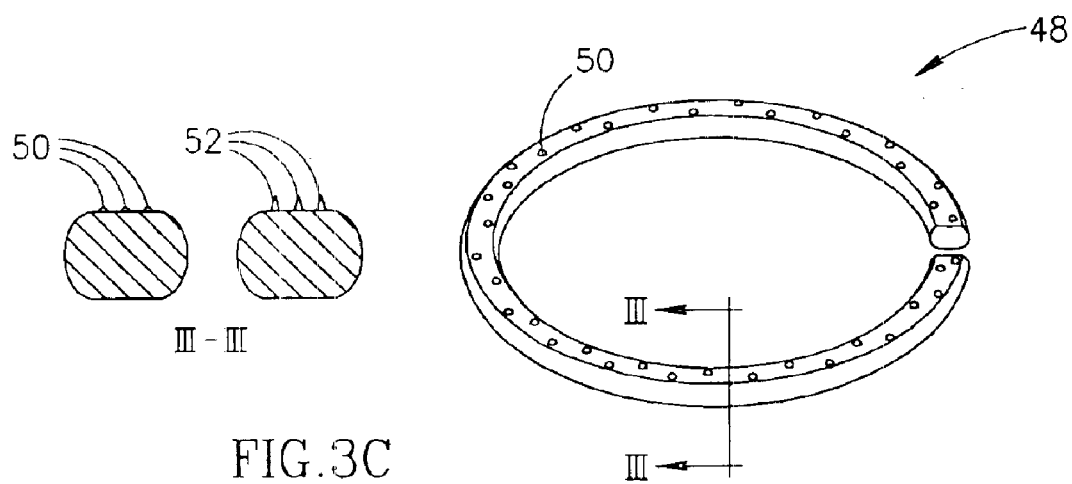

Further, to reduce the risk of the clip slipping against the wall tissue surfaces, the surface of the clip may be modified to provide an improved grip. Referring now to FIGS. 3A–3C, there is seen in FIG. 3A a partial-perspective view of a surgical clip referenced 40 and a cross-sectional view taken along line I—I of surgical clip 40, having a plurality of parallel grooves referenced 42 formed in the surface thereof, according to an alternative embodiment of the present invention. In FIG. 3B, there is seen a perspective and a partial perspective view of a surgical clip referenced 44 having a knurled surface referenced 46 formed therein, as seen in cross-sectional view II—II taken along line II—II, according to an alternative embodiment of the present invention. Referring also to FIG. 3C, there are seen a partial-perspective and cross-sectional views III—III taken along line III—III of a surgical clip referenced 48 having a plurality of studs referenced 50 or spikes referenced 52 formed in the surface thereof, according to an alternative embodiment of the present invention.

Any of the aforementioned sizes, shape configurations and surface modifications provide the surgeon with a plurality of alternatives, in accordance with embodiments of the present invention, dependent upon the particular organs to be joined, the relative sizes of the organs and the condition of the wall surfaces of the organs.

Figure 4:
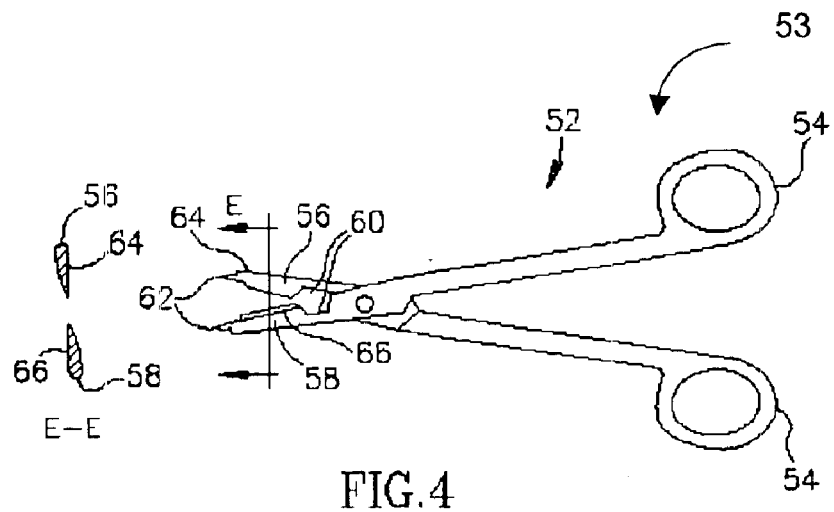
FIG. 4 illustrates an applicator device formed in a forceps configuration having scissors-type blade and counter elements.

Referring now to FIG. 4, there is illustrated an example of a scissors-type surgical clip applicator device generally referenced 52. Applicator device 52 is manually operated by handles referenced 54 at a proximal end, in relation to the user, thereof. At a distal end thereof are jaws referenced 56 and 58 having gripping apparatus including proximal fasteners referenced 60 and distal fasteners referenced 62 for gripping a surgical clip thereto (seen in FIGS. 8A and 8B, described hereinbelow). Situated between fasteners 60 and 62 there is seen formed in jaws 56 and 58 a pair of scissors-like cutting blades referenced 64 and 66 respectively, formed to act in cutting engagement to perforate, within the central opening of the surgical clip, tissue walls pressed together thereby. Cutting blades 64 and 66 can also be seen in a cross-sectional view taken along line I—I of jaws 56 and 58.

Figure 5:
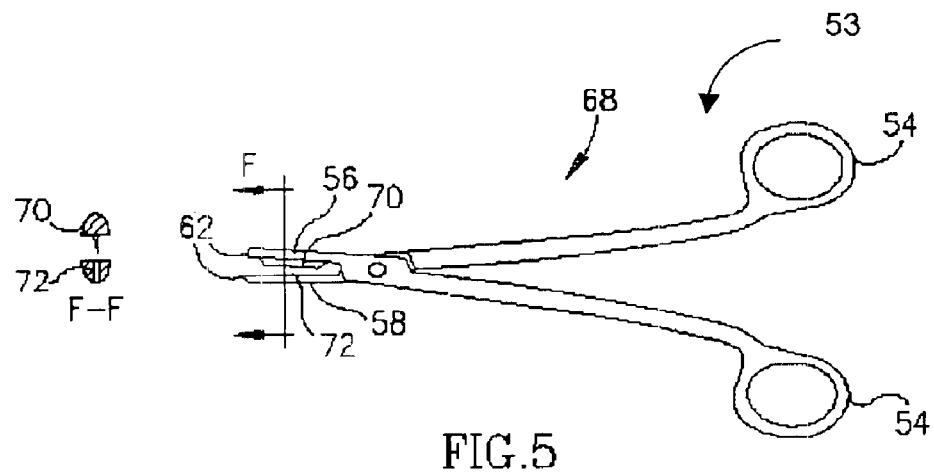
FIG. 5 illustrates an applicator device formed in a forceps configuration having blade and counter elements.
Figure 6:
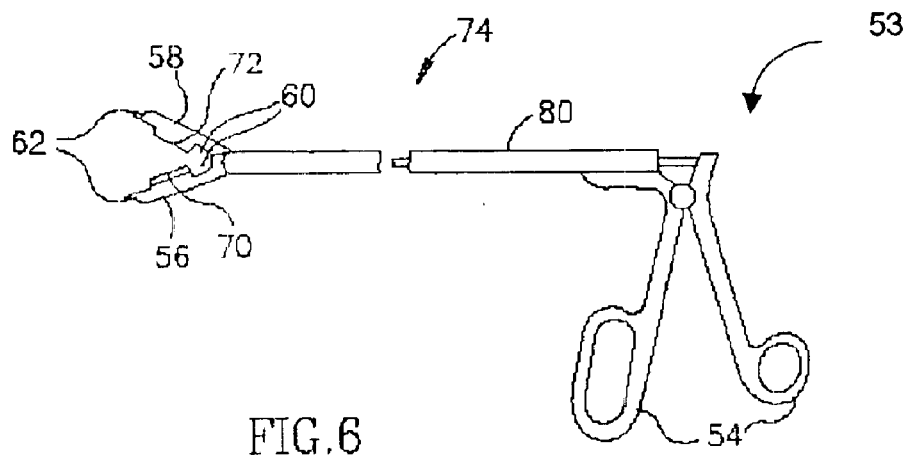
FIG. 6 illustrates an applicator device formed in an offset-forceps configuration for laproscopic-type applications having blade and counter elements.

Referring now to FIGS. 5 and 6, there are illustrated examples of forceps-type surgical clip applicator devices generally referenced 68 and 74 respectively. As indicated above, applicator devices 68 and 74 are manually operated by apparatus for activating, generally referenced 53, the apparatus including handles referenced 54 formed at a proximal end thereof. Applicator device 68 is generally for open surgery applications. Handles 54 are utilized to directly operate jaws 56 and 58 at the distal end of applicator device 68. Applicator device 74, generally for Laparoscopic-type applications, has apparatus for activating, generally referenced 53, including handles 54 in an off-set configuration with an extended pair of operating shafts referenced 80, sliding one within the other, to operate jaws 56 and 58. At a distal end of both applicator device 68 and 74, jaws referenced 56 and 58 have gripping apparatus including distal fasteners referenced 60 and proximal fasteners referenced 62 for gripping a surgical clip thereto (seen in FIGS. 8A and 8B referred to hereinafter). Situated between fasteners 60 and 62 there is seen, formed in jaw 56 a cutting blade referenced 70 and formed in jaw 58 a counter element referenced 72 acting as an anvil, formed to act in cuffing engagement to perforate, within the central opening of the surgical clip, tissue walls pressed together thereby. There is also seen a cross-sectional view taken along line F—F of jaws 56 and 58 indicating a cross-sectional view of cutting blade 70 and counter element 72 respectively.

While the blade and counter elements seen in FIGS. 4, 5 and 6 have specific configurations, it will be appreciated by persons skilled in the art that any suitable configuration of blade element and counter element may be employed. Tissue located therebetween and encircled by a surgical clip may be incised therethrough or partially cut away.

Referring now to FIGS. 7A–7H, there are illustrated examples of blade and counter element combinations, which are alternatives to those blade and counter elements seen in FIGS. 4, 5 and 6 and also, in FIGS. 8A–22A, as described hereinbelow.

Figure 7A:
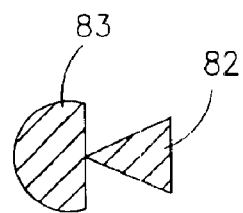
FIGS. 7A–7H illustrate cross-sectional views of examples of combinations of blade elements and counter elements as formed in an applicator device according to alternative embodiments of the present invention.
Figure 7B:
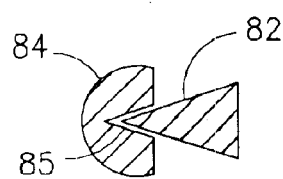
Figure 7C:
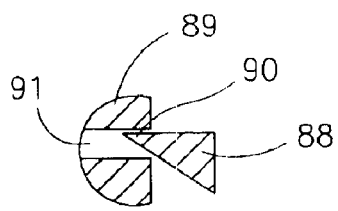
Figure 7D:
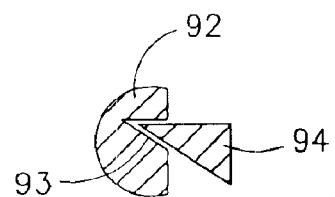

In FIG. 7A, there is seen a blade referenced 82 making contact with a flat-surfaced counter element referenced 83. Counter element 83 is formed having either a hard surface or a relatively soft surface such as a plastic polymer or other suitable material. In FIG. 7B, there is seen blade 82 and a counter element referenced 84 having a recess slot referenced 85 shaped to accommodate the edge of blade 82. In FIG. 7C, there is seen a blade referenced 88 and a counter element referenced 89 having a recess slot referenced 91 extending therethrough. Recess slot 91 is large enough to receive the edge 90 of blade 88. However, if blade 88 is moved further into recess slot 91, any further movement will be prevented when the width of blade 88, entering recess slot 91 is equal to the width of recess slot 91. Referring now to FIG. 7D, there is seen a counter element referenced 92 having a recess slot referenced 93 having a triangular cross-section, so formed to accommodate the edge of blade 94.

Figure 7E:
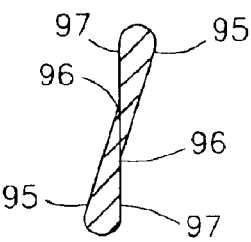

Further, referring to FIG. 7E, there is seen a combination of a pair of blade elements generally referenced 95 (similar to cutting blades 64 and 66 of FIG. 4) as an alternative to the aforementioned blade element and counter element combinations. Blade elements referenced 95 come into mutual contact in a scissors-like movement, such that an edge referenced 96 of each blade 95 lies adjacent to a side surface referenced 97 of the other blade 95.

Figure 7F:
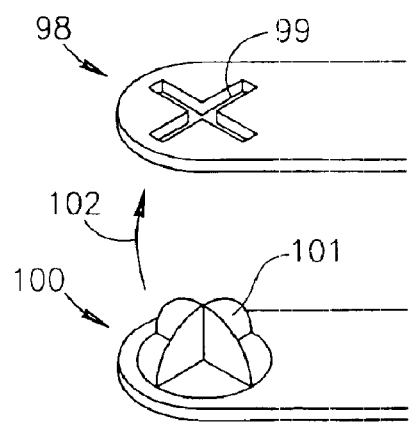

Referring now to FIG. 7F, there is seen a partial perspective view of a counter element, referenced generally 98, and of a blade element, referenced generally 100. Counter element 98 is provided with an X-shaped aperture 99, which corresponds in configuration and size to blade 101 of blade element 100. Thus, when employing counter element 98 and blade element 100 in an applicator device of the present invention, when the intermediate portion of the clip is in an elastic state, as disclosed herein below, counter element 98 and blade element 100 are pressed together in the direction of arrow 102. This forces blade 101 into aperture 99, thereby perforating the tissue therebetween.

Figure 7G:
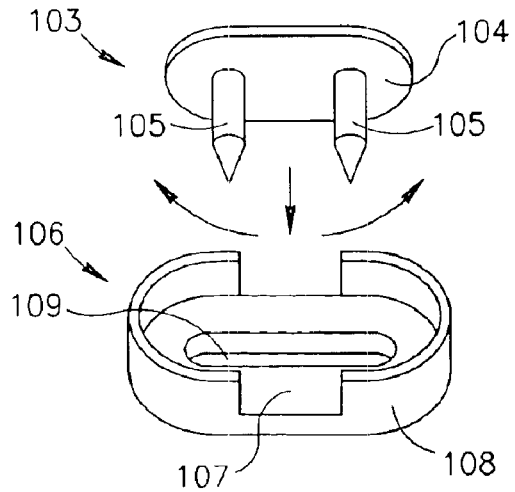

There is further seen in FIG. 7G a blade element generally referenced 103 and a corresponding counter element generally referenced 106. Blade element 103 is provided with an elliptically shaped base portion referenced 104 having a pair of needle-like blades referenced 105 protruding therefrom. Counter element 106 is provided with an elliptically shaped base portion referenced 107, similar in configuration and size to base portion 104 of blade element 103, and a flange 108 extending therefrom. Base portion 107 also has an elliptical aperture 109, of a similar width to that of blades 105 and having a length at least equal to the external distance from one needle-like blade to the other. Thus, when employing counter element 106 and blade element 103 in the applicator device of the present invention, counter element 106 and blade element 103 are pressed together, forcing blades 105 into aperture 109, thereby perforating the tissue therebetween.

Figure 7H:
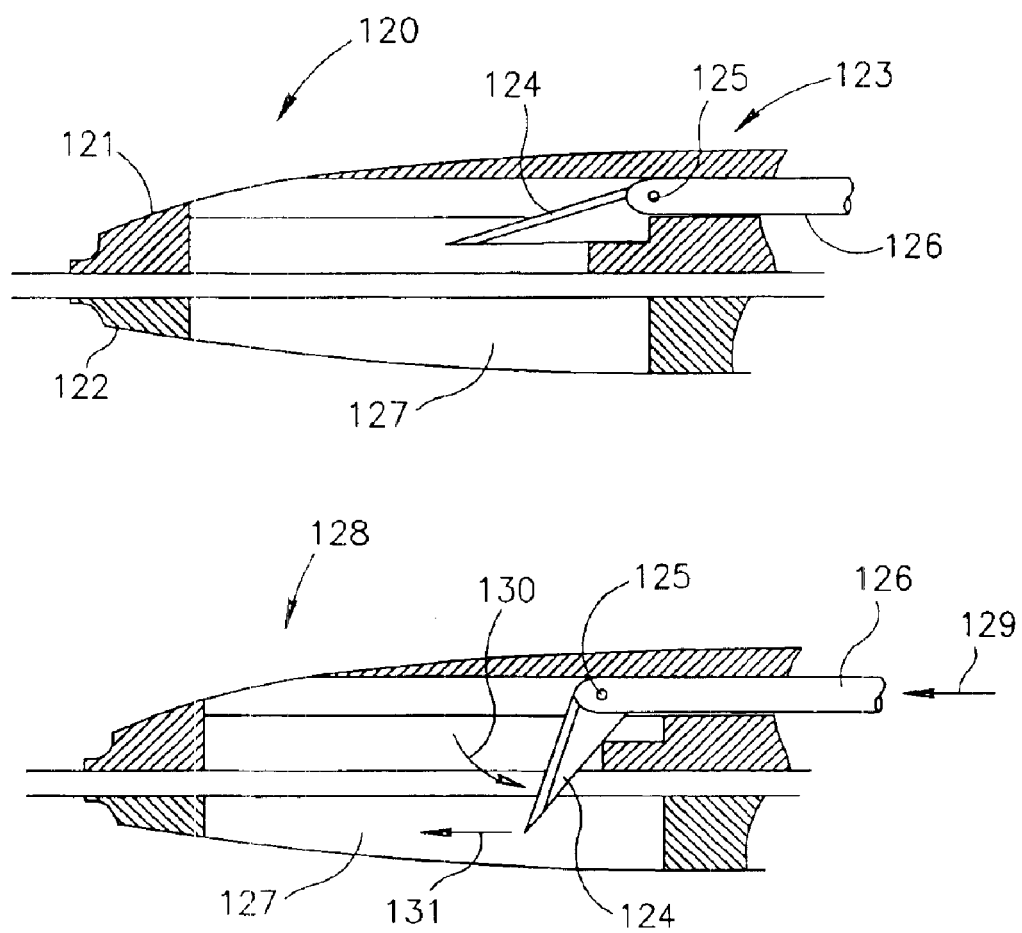

In FIG. 7H, there is seen a partial cross-sectional view, prior to operation, of a distal portion generally referenced 120 of an anastomosis clip applicator device, including jaws referenced 121 and 122, seen in a closed configuration. In normal usage, jaws 121 and 122 are closed to press together adjacent hollow organ walls (not shown) and to engage a clip 10 (FIG. 1) thereto. Jaw 121 is formed having a blade element generally referenced 123 and jaw 122 is formed having a counter element referenced 127 formed as a slot. Blade element 123 includes a blade referenced 124, which is pivotally attached at a pivot referenced 125 to an operating shaft referenced 126. Further, there is depicted the operation of distal portion generally referenced 128. To perforate the adjacent wall portions pressed together by jaws 121 and 122 and by ring 10 (not shown), shaft 126 is advanced in the direction indicated by arrow 129. This movement causes blade 124 to rotate about pivot 125, as indicated by arrow 130 and to protrude into slot 127, thereby to puncture the adjacent organ wall portions (not shown). Further advancing shaft 126 results in blade 124 advancing as indicated by arrow 131, cutting through the adjacent organ wall portions. To withdraw blade 124 from the cut through wall portions, shaft 126 is withdrawn to the starting position prior to the operation, causing blade 124 to return to its initial position.

Figure 8A:
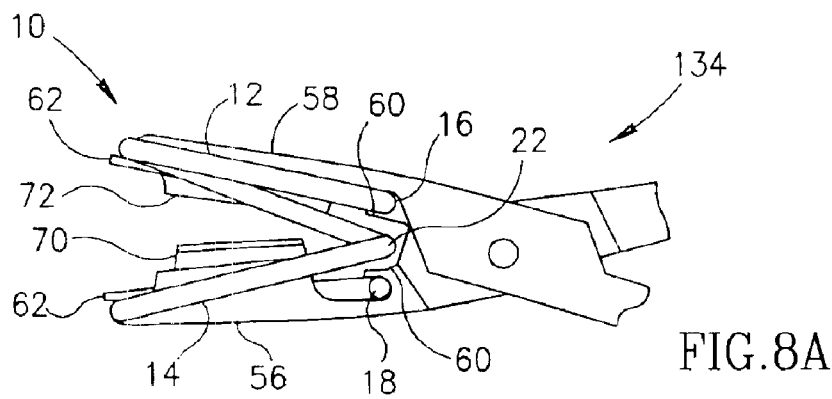
FIGS. 8A–8C illustrate partial and perspective partial views of a forceps applicator device having a surgical clip operatively attached thereto.
Figure 8B:
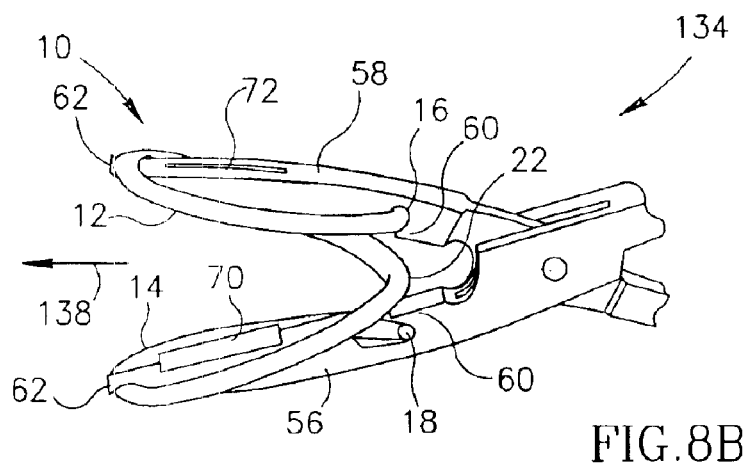

Referring now to FIGS. 8A and 8B, there is seen a surgical clip referenced 10 operatively attached to jaws referenced 56 and 58 of forceps generally referenced 134. More specifically, ends 16 and 18 of clip 10 are held in position by proximal fasteners referenced 60 and loops 12 and 14 of clip 10 are held in position by distal fasteners referenced 62. Clip 10 is seen in an open position, having intermediate portion 22 in a plastic state while the temperature thereof is below a transition temperature. The change in temperature, as it affects the shape memory alloy portion 22 of clip 10, will be discussed further hereinbelow, with reference to FIGS. 22A–22D.

After clip 10 has been inserted to join two organ portions as related hereinbelow, with reference to FIGS. 22A–22D, the temperature of intermediate portion 22 rises above the transition temperature. Thereupon, loops 12 and 14 of clip 10 close and press on adjacent walls of hollow organ portions. After perforating the wall portions held within clip 10 using blade 70 and counter element 72, clip 10 is released from fasteners 60 and 62 by manually pushing clip 10 distally forward in the direction indicated by arrow 138 (FIG. 8B). This causes disengagement of ends 16 and 18 from proximal fasteners 60 and of loops 12 and 14 from distal fasteners 62.

Figure 8C:
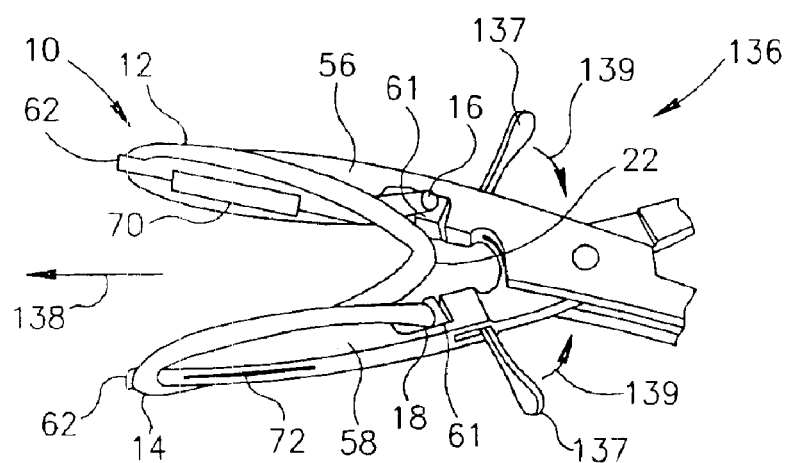
Figure 10C:
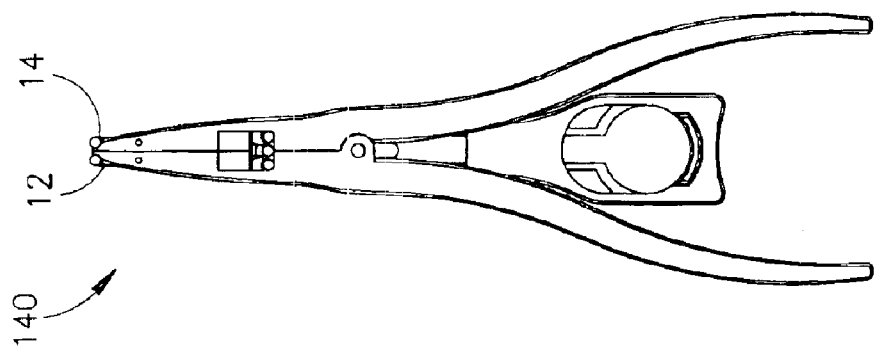
Figure 10B:
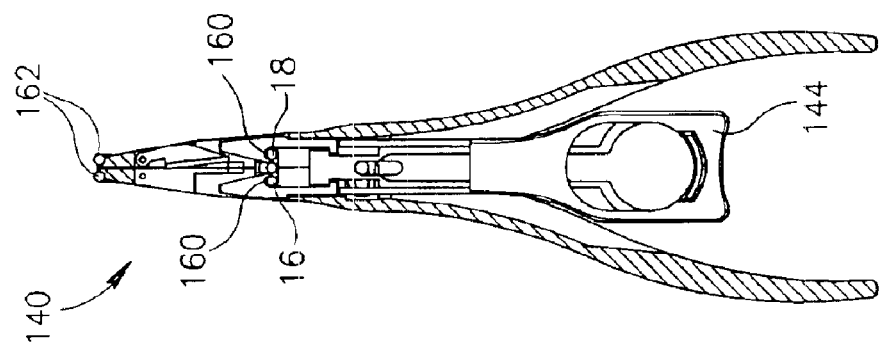
Figure 10A:
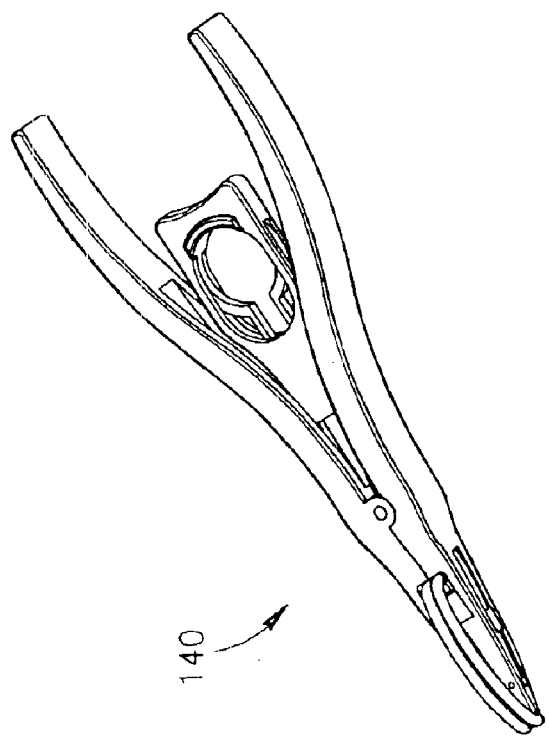
Figure 11C:
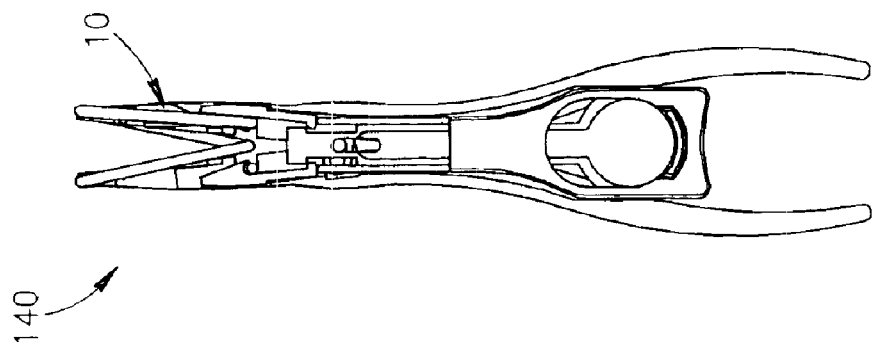
Figure 11B:
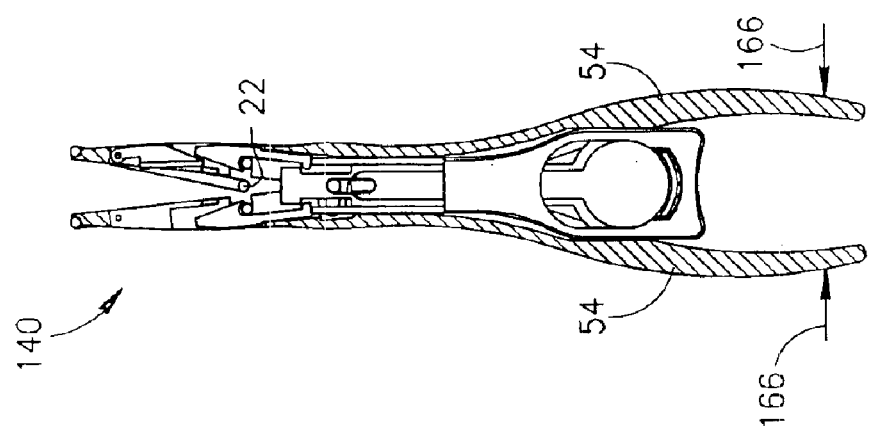
Figure 11A:
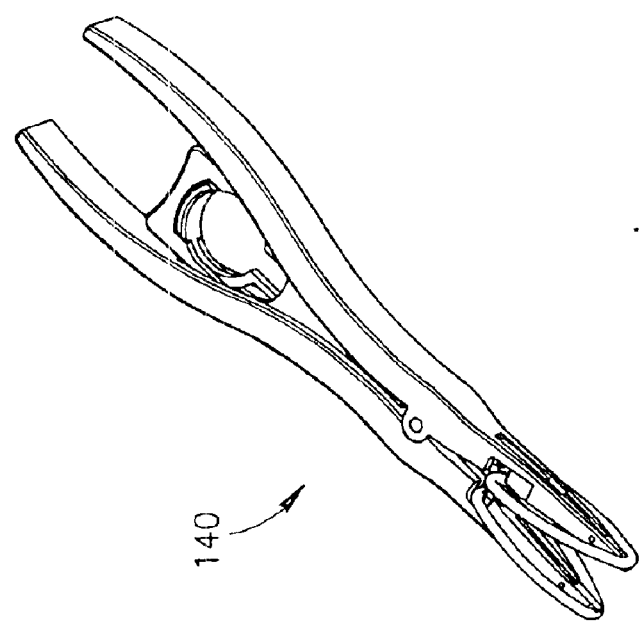

Referring now to FIG. 8C, there is seen a surgical clip referenced 10 operatively attached to jaws referenced 56 and 58 of forceps referenced 136. More specifically, ends 16 and 18 of clip 10 are held in position by proximal fasteners referenced 61 and loops 12 and 14 are held in position by distal fasteners referenced 62 with levers referenced 137 in the positions indicated. After clip 10 assumes a closed position pressing together adjacent organ walls, clip 10 is released and ejected from fasteners 61 and 62 in the direction indicated by arrow 138 by moving levers 137 in the direction indicated by arrows 139 and, thereafter, returning levers 137 to the positions indicated.

Referring now to FIGS. 9–14, there is illustrated a sequence of operating stages of a pliers-type surgical clip applicator device generally referenced 140, seen in perspective, full and cross-sectional views. In FIG. 9, apparatus for activating, generally referenced 153, includes handles referenced 54, external ring referenced 144 and loading ring referenced 146. After inserting clip 10 into opened jaws referenced 156 and 158 while holding the handles 54, fasteners 160 engage ends 16 and 18 and fasteners 162 engage loops 12 and 14. Loading ring referenced 146 is pulled in the direction indicated by arrow 142 to lock clip to pliers 140 as seen in FIGS. 10A–10C, external ring referenced 144 remaining in the position indicated.

At this stage, clip 10 or at least the intermediate portion 22 is cooled to below the transition temperature, causing portion 22 to assume a plastic state. Thereupon, by pressing handles 54 in the direction indicated by arrows 166 in FIGS. 11A–11C, clip 10 is opened in readiness for insertion into position into adjacent organ portions to be joined by anastomosis (as related hereinbelow in relation to FIGS. 22A–22D). Until insertion, portion 22 of clip 10 is maintained at a temperature below the transition temperature.

Figure 12C:
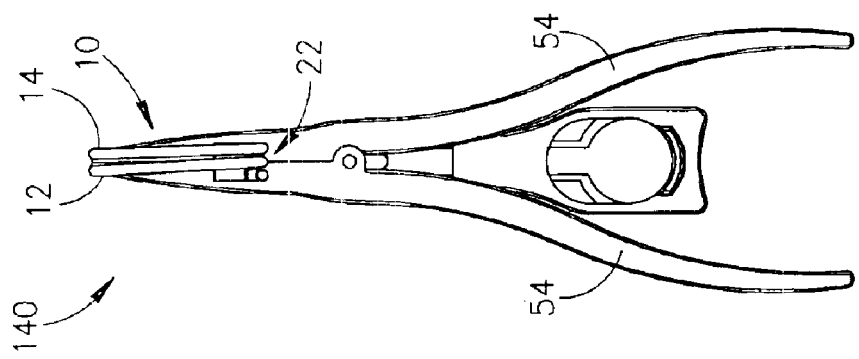
Figure 12B:
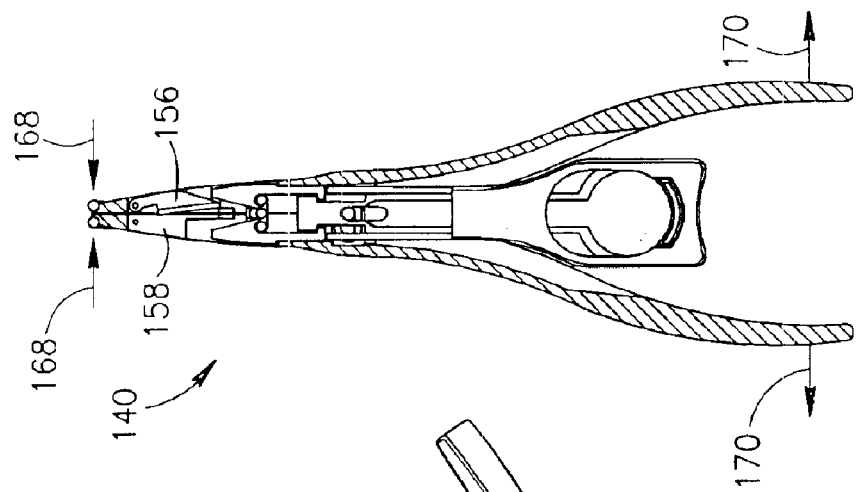
Figure 12A:
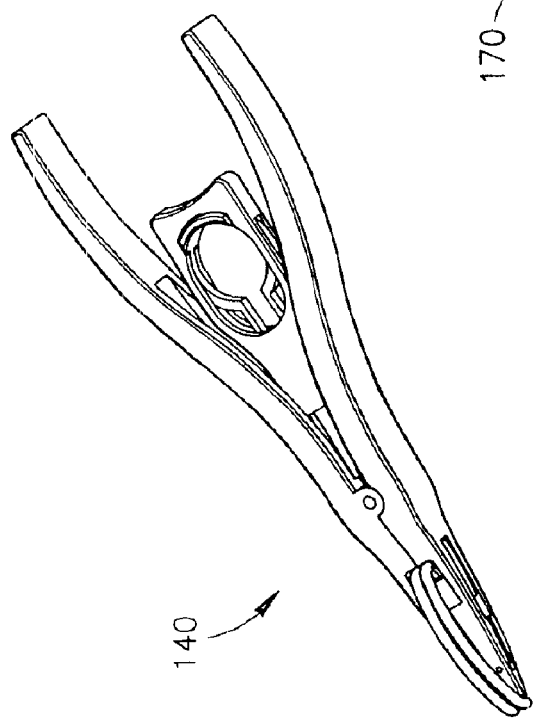
Figure 13B:
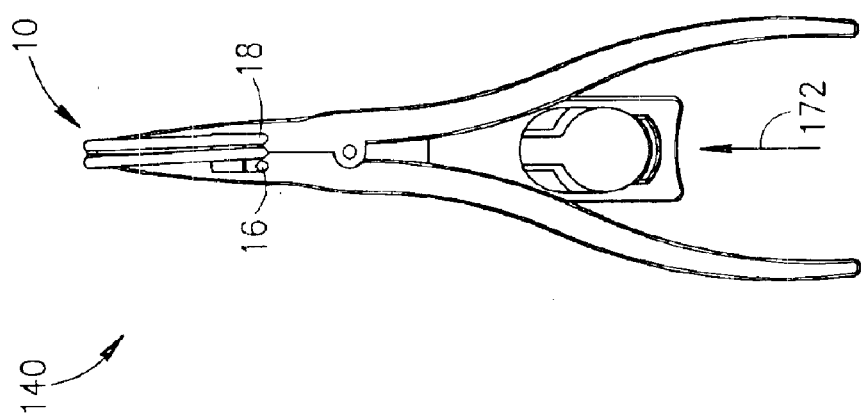
Figure 13A:
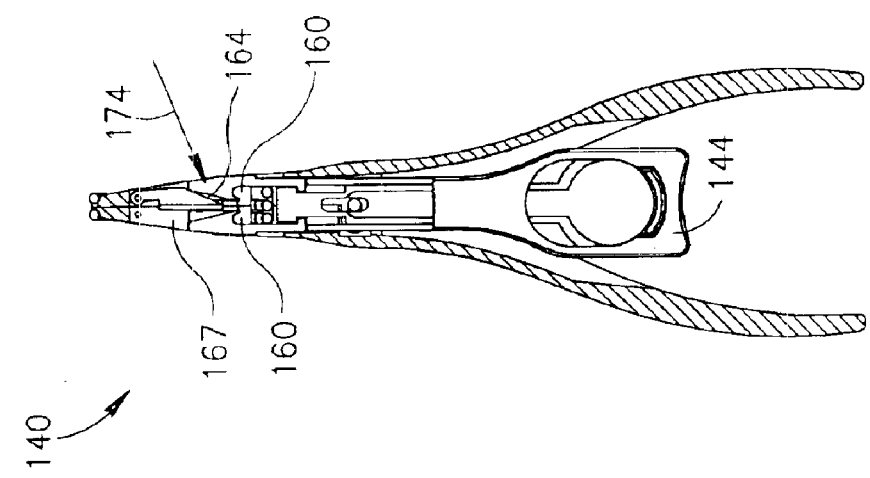
Figure 14C:
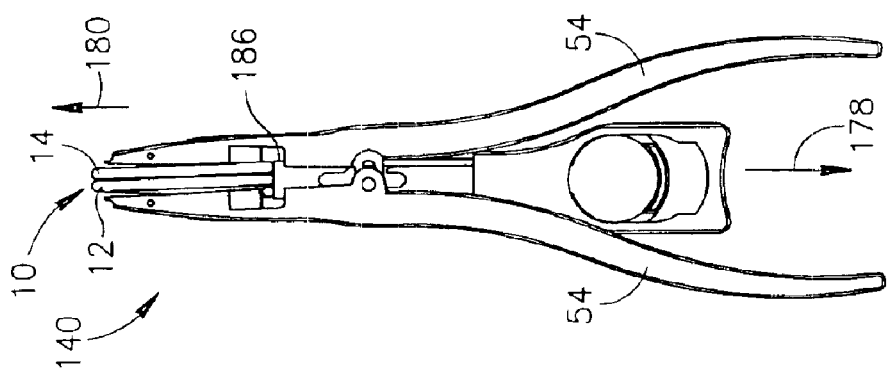
Figure 14B:
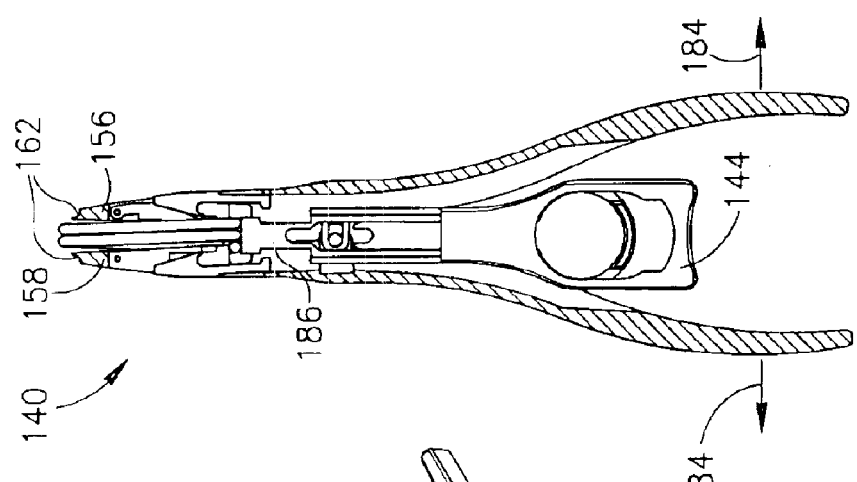
Figure 14A:
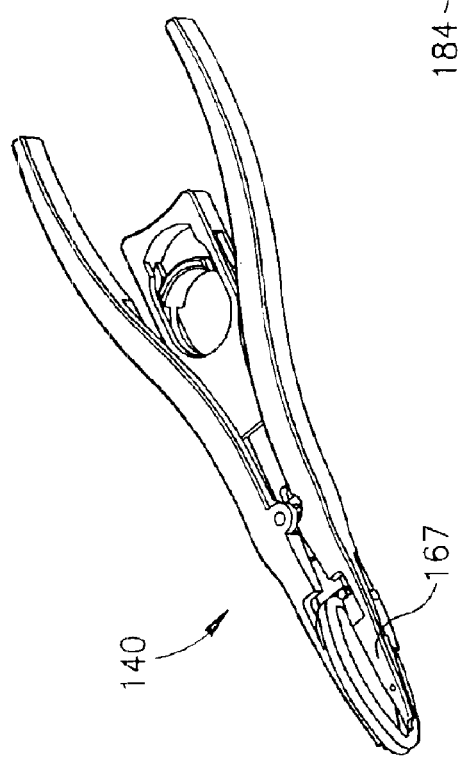

As seen in FIGS. 12A–12C, once clip 10 has been inserted into position, handles 54 are drawn apart as indicated by arrows 170 causing jaws 156 and 158 to move together as indicated by arrows 168. As the temperature of portion 22 of clip 10 rises above the transition temperature, rings 12 and 14 press against the adjacent organ wall portions. At this point, as indicated in FIGS. 13A and 13B, external ring 144 is pushed in the direction indicated by arrow 172, causing blade 164 to rotate in the direction indicated by arrow 174. Blade 164 in cutting engagement with counter element referenced 167, cuts through the adjacent walls pressed together by closed clip 10, creating initial patency of the gastrointestinal tract. Simultaneously, ends 16 and 18 of clip 10 are released from fasteners 160. Finally, as indicated in FIGS. 14A–14C, by pulling external ring 144 in the direction indicated by arrow 178, pliers handles 54 move apart as indicated by arrows 184. Also, ejector 186 pushes clip 10 in the direction indicated by arrow 180, causing loops 12 and 14 to disengage from fasteners 162 and jaws 156 and 158 to open.

Referring now to FIGS. 15–19, there is illustrated a sequence of operating stages of a palm-held, tong-type, hand operated laparoscopic surgical clip applicator device generally referenced 200. Laparoscopic surgical clip applicator device 200 includes apparatus for activating, generally referenced 203, which includes handle referenced 206, guide lever referenced 208, ratchet pin referenced 209, and ratchet rod referenced 215. Applicator device 200 is sequence operated by repeatedly depressing and releasing handle 206 which pushes a guide lever 208 having a ratchet pin 209. Each time handle 206 is depressed, ratchet pin 209, initially positioned in notch referenced 210, advances ratchet rod 215 and as handle 206 is released, succeeding notches referenced 211, 212, 213 and 214 are successively engaged. As ratchet rod 215 advances, cam-pins 218 traverse jaw-cam-slots referenced 226 so as to cause jaws referenced 219 and loops 12 and 14 of clip 10 attached to distal fasteners referenced 217, to move apart or together in accordance with the profile of jaw-cam-slots 226. Simultaneously, cam-pins 218 traverse internal-jaw slots referenced 223 formed in internal jaws referenced 221, in accordance with the profile of internal jaw-slots 223, as to open or close internal jaws 221 and to open ends 16 and 18 of clip 10 gripped by proximal fasteners referenced 216. Cutting blade referenced 224 and counter element referenced 225, formed as a slot, are configured to operate in a cutting engagement, as pin 218 advances as related hereunder.

Figures 15A, 15B, 15C:
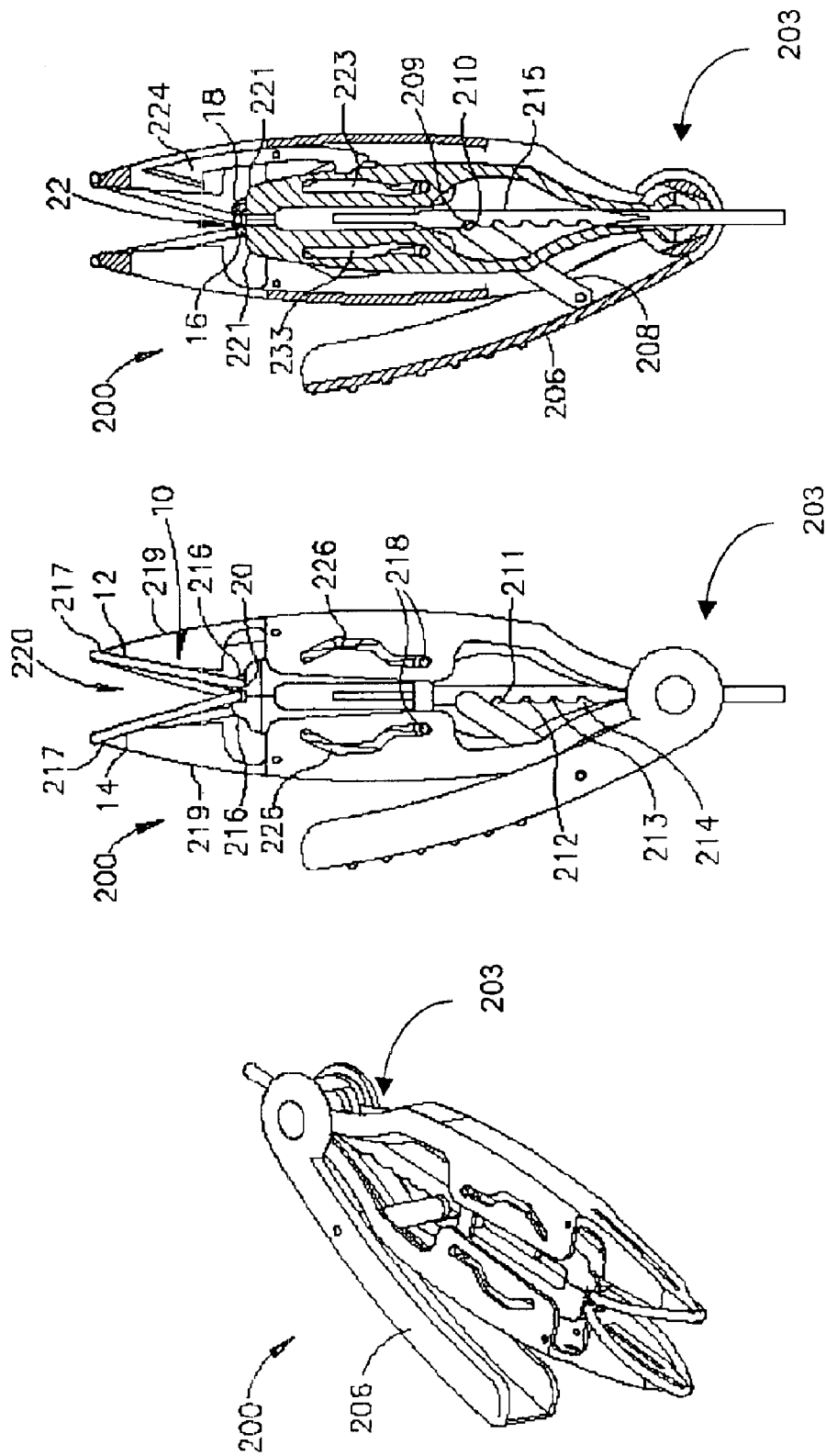

In FIGS. 15A–15C there is depicted Operating Step 1 in which applicator device 200 has jaws 219 open having a distal gap referenced 220 between distal fasteners 217, distally formed on jaws 219. Clip 10, or at least intermediate portion 22 thereof, is cooled below the transition temperature. Loops 12 and 14 are manually opened and attached to distal fasteners 217 and ends 16 and 18 are attached to proximal fasteners 216, with ratchet pin 209 engaging ratchet slot 210 in the initial position.

Operative Step 2 is carried out while maintaining a temperature below the transition temperature, as depicted in FIGS. 16A and 16B. After depressing and releasing handle 206 and thereupon ratchet pin 209 engaging ratchet slot 211, internal jaws 221 are caused to move apart as indicated by arrows 234 so as to spread ends 16 and 18. This provides the operating surgeon with improved access to the adjacent organ walls to be joined, close to midpoint 20 of clip 10, after inserting jaws 219 into the adjacent organ portions.

Figure 17B:
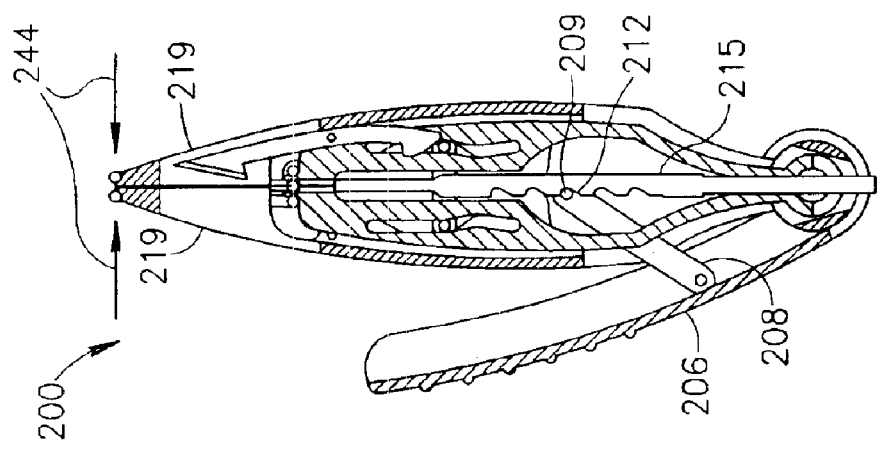
Figure 17A:
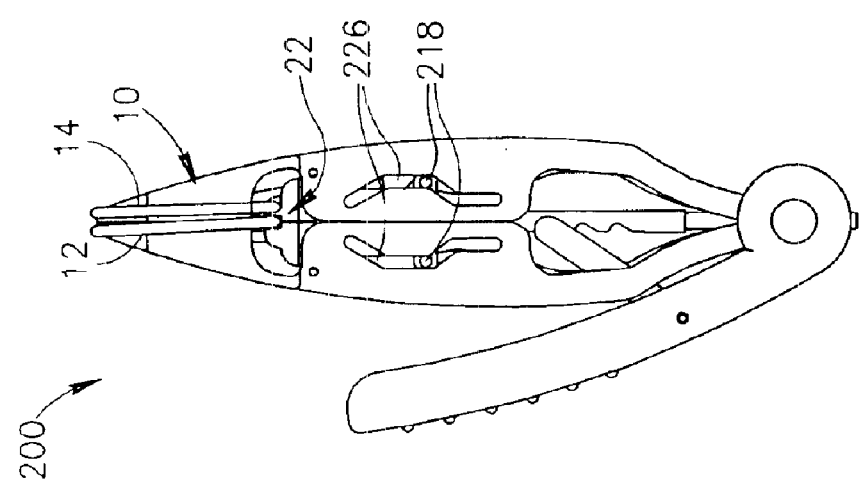

When applicator device 200 is properly inserted into adjacent organ portions so that clip 10 is positioned to engage adjacent wall portions, Operative Step 3 follows as seen in FIGS. 17A and 17B. Handle 206 is once again depressed and released, advancing ratchet rod 215, and engaging pin 209 into slot 212. Thereupon, jaws 219 assume a closed position as indicated by arrows 244 and clip 10 presses the adjacent organ wall portions together as the temperature of intermediate portion 22 is allowed to rise above the transition point.

Figure 18B:
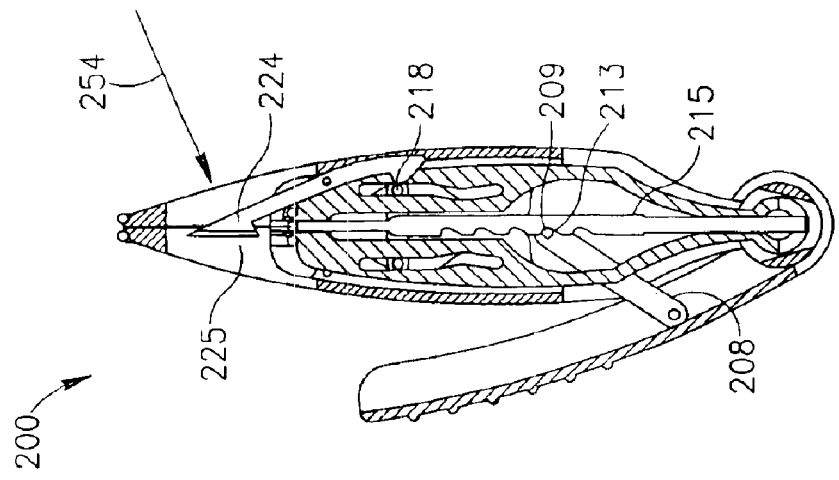
Figure 18A:
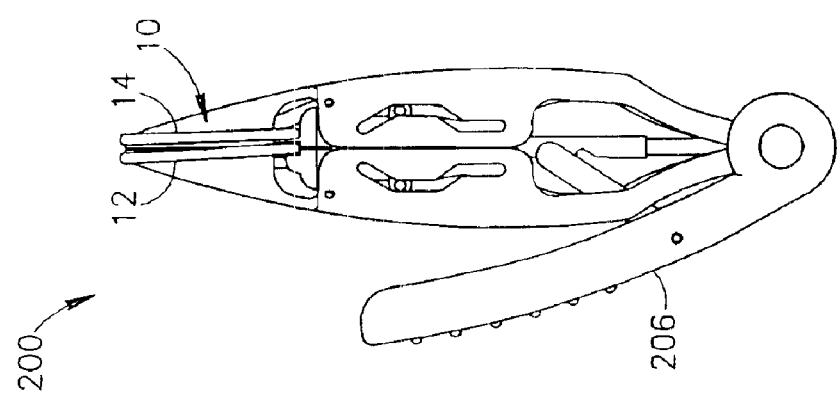

Operative Step 4 follows as seen in FIGS. 18A and 18B. Handle 206 is again depressed and released, pin 209 engaging slot 213 and advancing ratchet rod 215. This causes cam-pin referenced 218 to advance which, in turn, causes blade 224 to rotate in the direction indicated by arrow 254 into counter element 225, so as to cut through the wall portions pressed between loops 12 and 14 of clip 10, creating initial patency of the gastrointestinal tract.

Figure 19B:
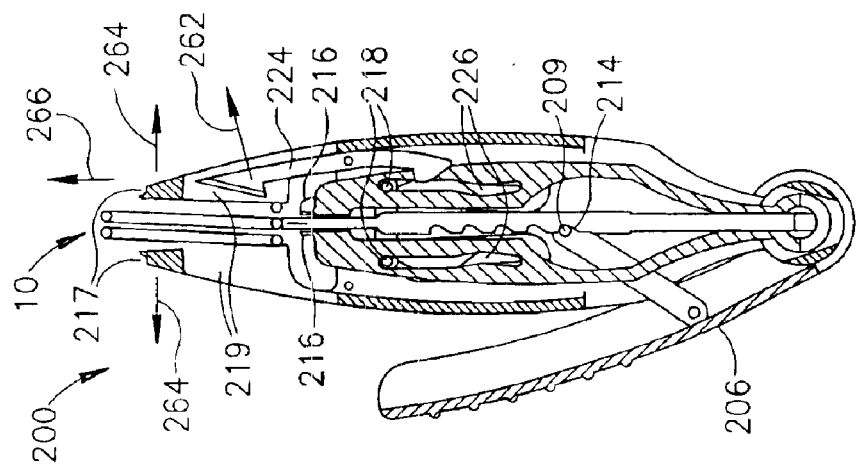
Figure 19A:
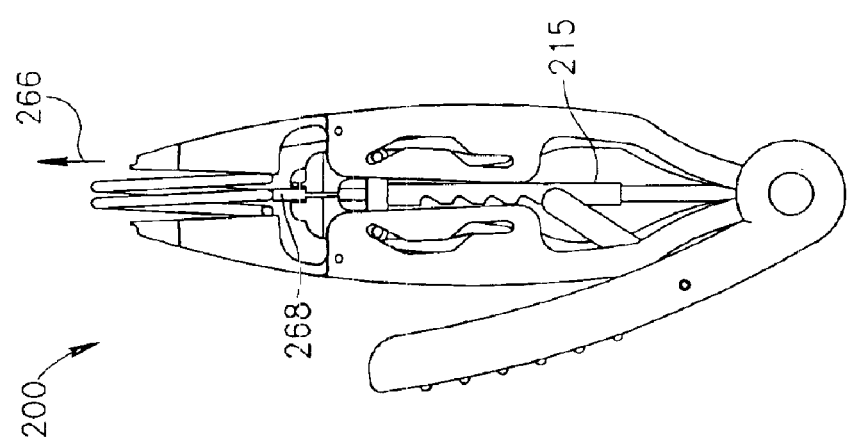

In FIGS. 19A and 19B, Operative Step 5 is depicted after a final depression and release of handle 206, resulting in engagement of pin 209 with slot 214 and a further advance of ratchet rod 215 such that cam-pins 218 reach the distal end of jaw-cam slots 226. An ejection pin referenced 268 formed at the distal end of ratchet rod 215, ejects clip 10 in the direction indicated by arrow 266. Simultaneously, blade 224 is retracted as indicated by arrow 262 and jaws 219 move slightly apart as indicated by arrows 264 to facilitate ejection of clip 10 from fasteners 216 and 217. Thereafter, applicator device 200 is withdrawn from the organ portions, leaving clip 10 in position.

Figure 20C:
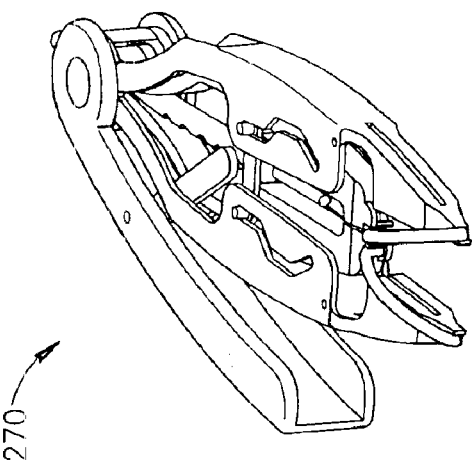
FIGS. 20A–20C illustrate a full, partial cross-sectional and perspective view of a manually-sequential surgical clip applicator device for open surgery anastomosis, having a surgical clip operatively attached thereto, wherein blade and counter elements are replaced with a pair of blade elements, according to an alternative embodiment of the present invention.
Figure 20B:
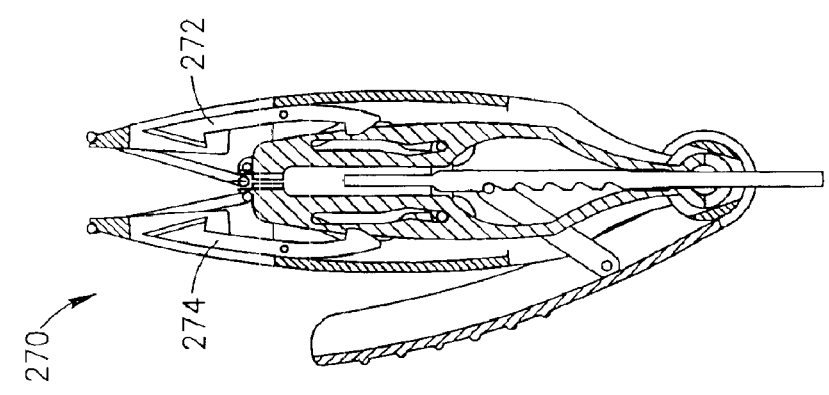
Figure 20A:
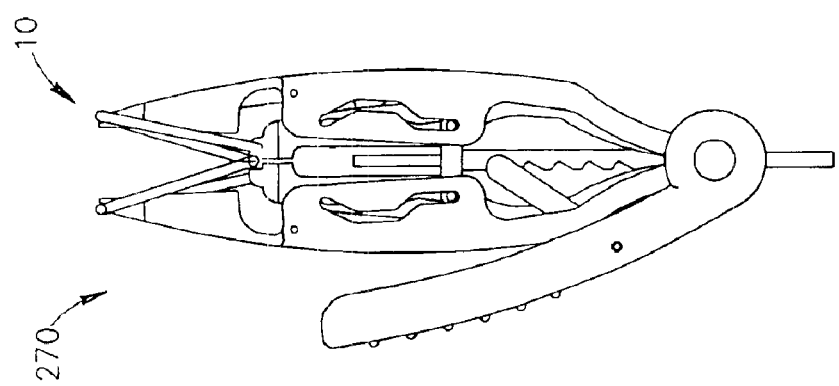

Referring now to FIGS. 20A–20C, there is illustrated in accordance with an alternative embodiment of the present invention, a hand operated laparoscopic surgical clip applicator device generally referenced 270, wherein blade element 224 and counter element 225 (FIGS. 15A–19B), are replaced by a pair of blade elements referenced 272 and 274, respectively. Blade elements 272 and 274 operate to cut through the adjacent wall portions pressed together by clip 10 in a scissors-like action.

The blade and counter elements seen in FIGS. 9A–20C have specific configurations. It will be appreciated by persons skilled in the art that any suitable configuration of blade element and counter element, such as seen in FIGS. 7A–7H, may be employed, whereby tissue located therebetween and encircled by a surgical clip may be incised therethrough or partially cut away.

Referring now to FIGS. 21A–21D, there is seen an anastomosis clip applicator device generally referenced 280 having a proximal handle portion generally referenced 281 and a detachable distal portion generally referenced 282. Proximal portion 281 and distal portion 282 are held together by locking levers referenced 284. Applicator device 280 in operational association with, for example, surgical clip 10, is generally utilized in a similar manner to that discussed hereinbelow, with reference to FIGS. 22A–22D, to join organ portions 304 and 306.

Figure 21A:
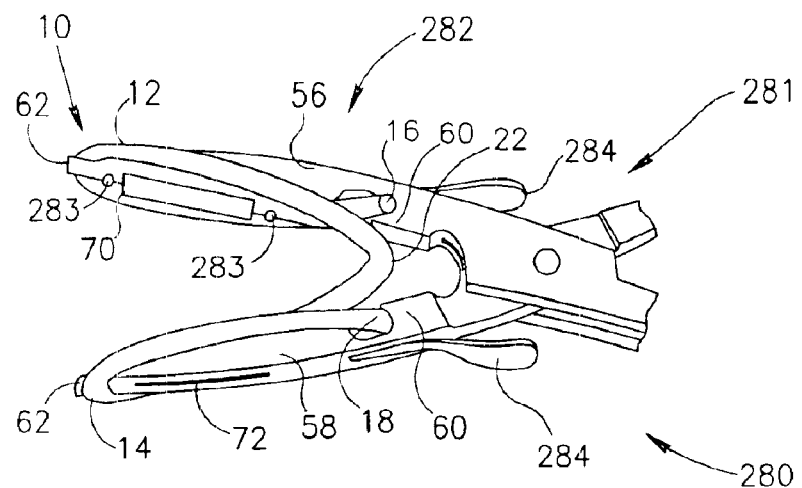
FIGS. 21A–21E illustrate partial perspective, pictorial and cross-sectional views of a surgical clip applicator device having a detachable distal portion.
Figure 21B:
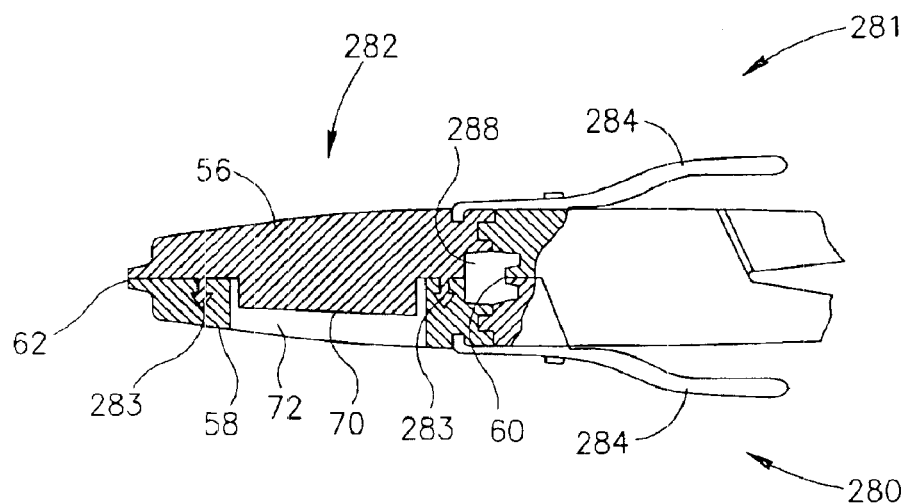
Figure 21C:
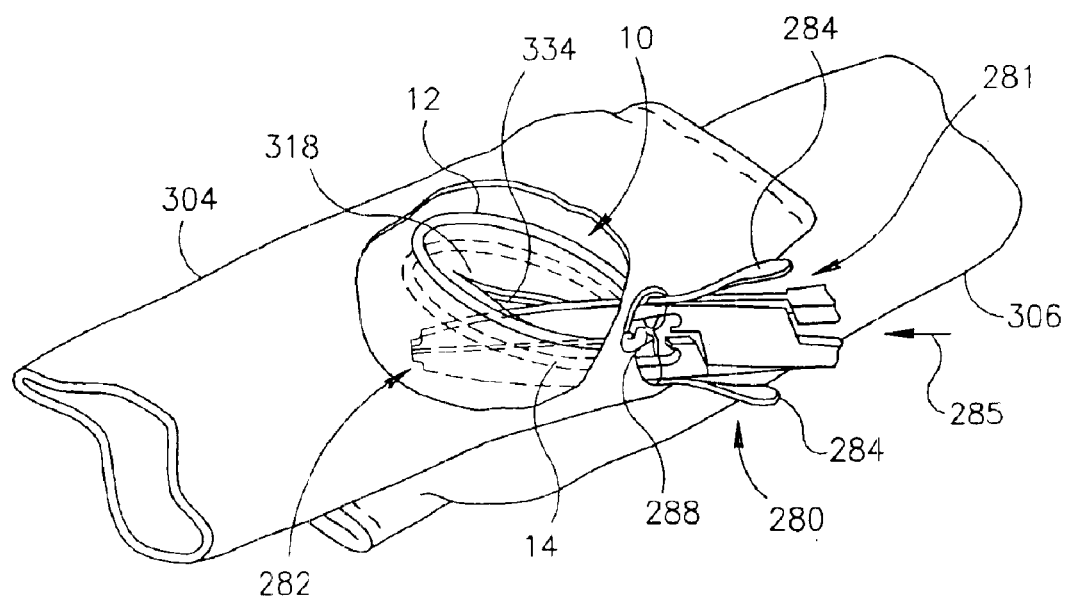
Figure 21D:
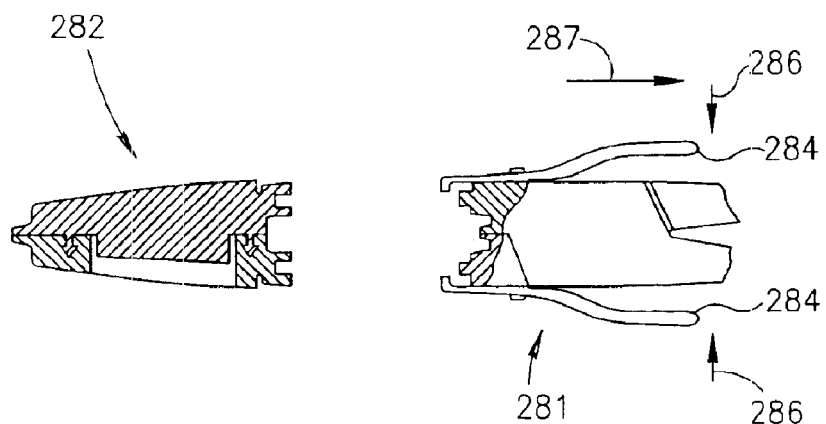

Clip 10 (not shown) is attached to distal portion 282. Ends 16 and 18 of clip 10 are attached to proximal fasteners 60 and loops 12 and 14 of clip 10 are attached to distal fasteners 62 of jaws 56 and 58, respectively. After jaws 56 and 58 and loops 12 and 14 of clip 10 are closed to press together against the adjacent organ wall portions 318, a cut 334 is made therethrough with cutting blade 70 and counter element 72. Also, jaws 56 and 58 are fastened together by engaging locking elements referenced 283. Thereafter, loops 12 and 14 of clip 10 are disengaged from fasteners 62 and ends 16 and 18 are disengaged from fasteners 60 by ejecting clip 10 in a distal direction. Loops 12 and 14 and ends 16 and 18 are closed against the adjacent organ walls and together remain held in opening 288 (FIG. 21B). By slightly withdrawing applicator device 280, distal portion 282 is pushed in the direction indicated by arrow 285 (FIG. 21C) through cut 334 into organ portion 306 (FIG. 21C). By pressing levers 284 in the direction indicated by arrows 286 (FIG. 21D), distal portion 282 is detached from proximal portion 281, which is then withdrawn in the direction indicated by arrow 287 (FIG. 21D). Distal portion 282 remains in organ portion 306 to be passed through the gastrointestinal tract.

Figure 21E:
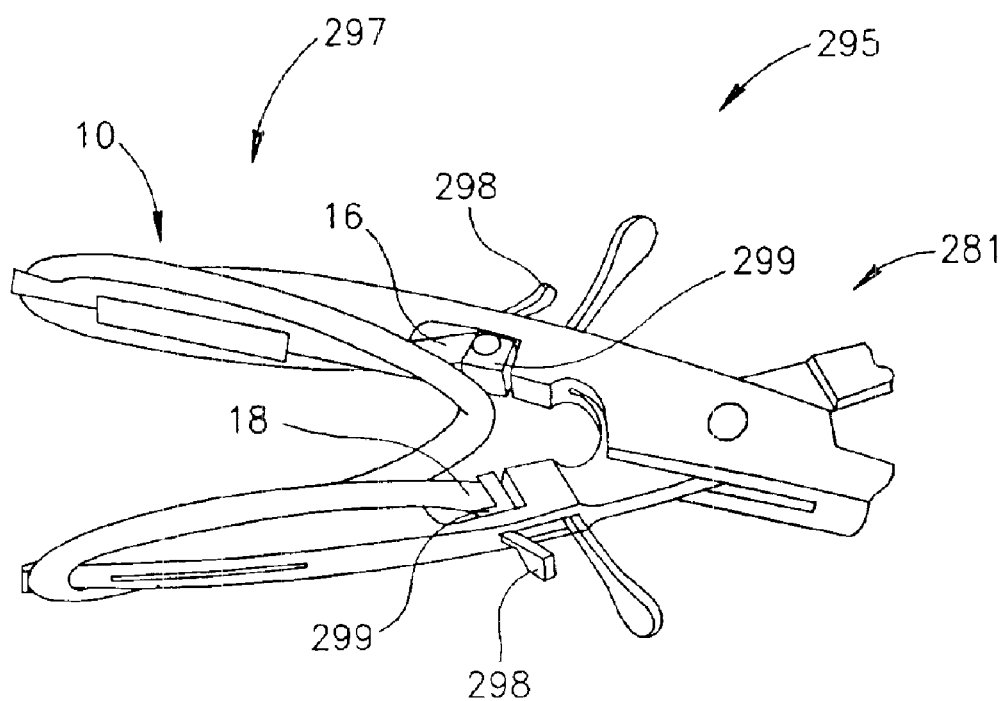

Referring now to FIG. 21E, there is seen an applicator device generally referenced 295, alternative to applicator device 280 (FIGS. 21A–21D), insofar as proximal portions 281 are essentially similar. However, distal portion referenced 297 of applicator device 295 includes locking levers referenced 298 and locking fasteners referenced 299 to lock ends 16 and 18 of clip 10 in position and to facilitate ejecting clip 10 therefrom.

In accordance with another embodiment of the present invention, there is apparatus for activating the gripping apparatus, release mechanism and cutting apparatus, so as to introduce and apply the surgical clip into adjacent hollow organ portions. This apparatus may be a mechanical, pneumatic, hydraulic or electrical activator means, which may be remotely operated.

Figure 22A:
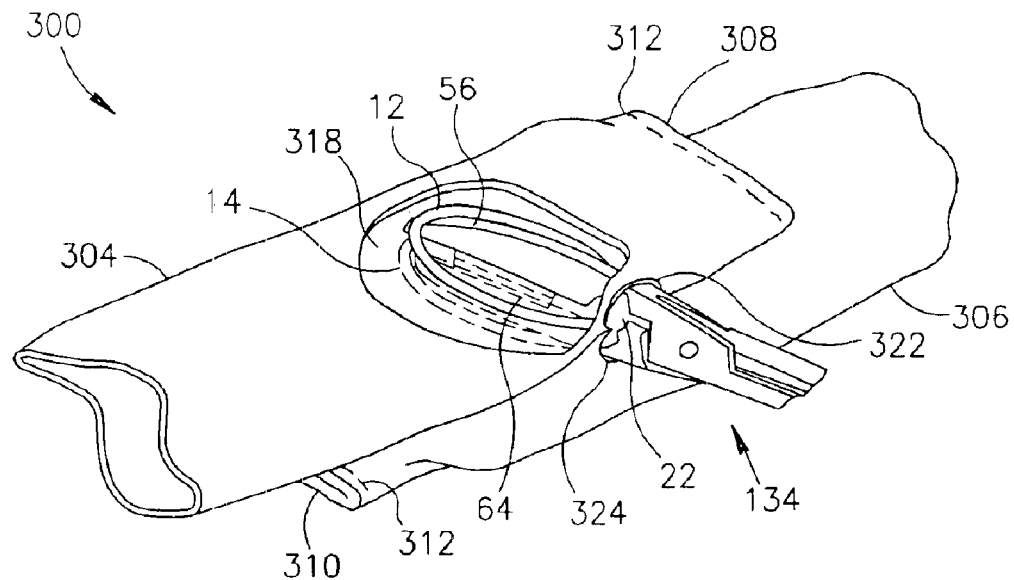
FIGS. 22A–22D illustrate pictorial and cross-sectional views depicting a procedure for joining portions of a hollow organ, using a surgical clip applicator device and a surgical clip.
Figure 22B:
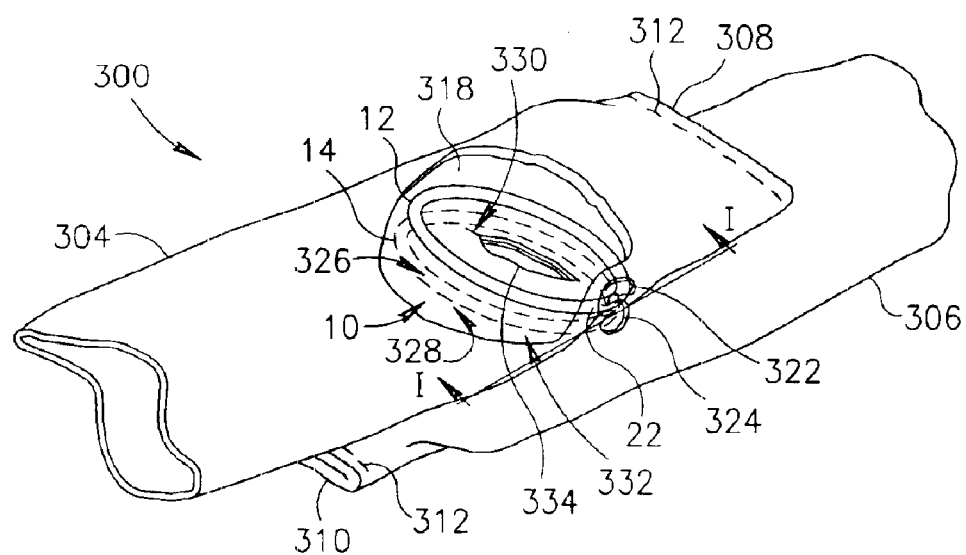
Figure 22C:
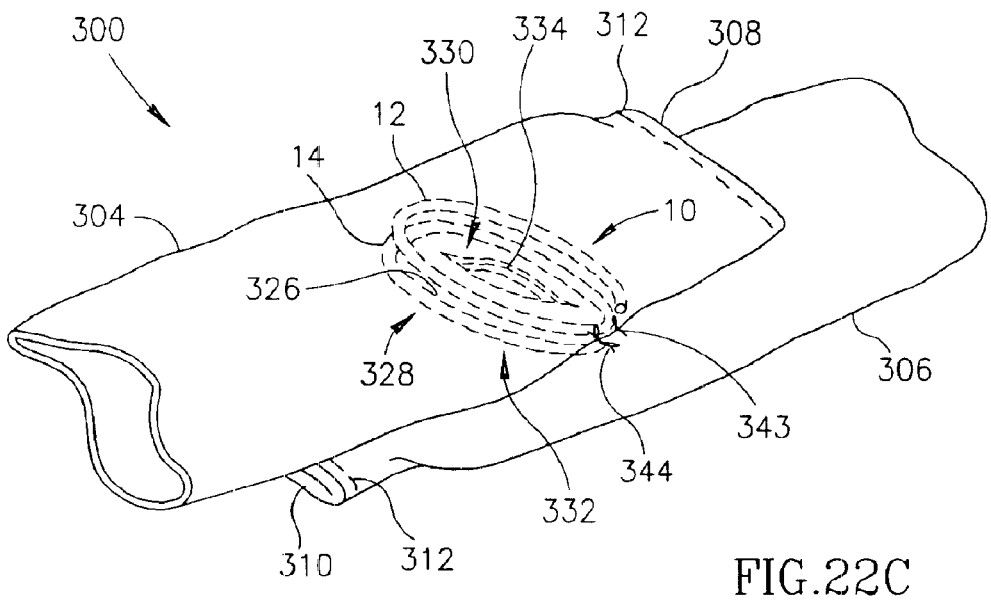
Figure 22D:
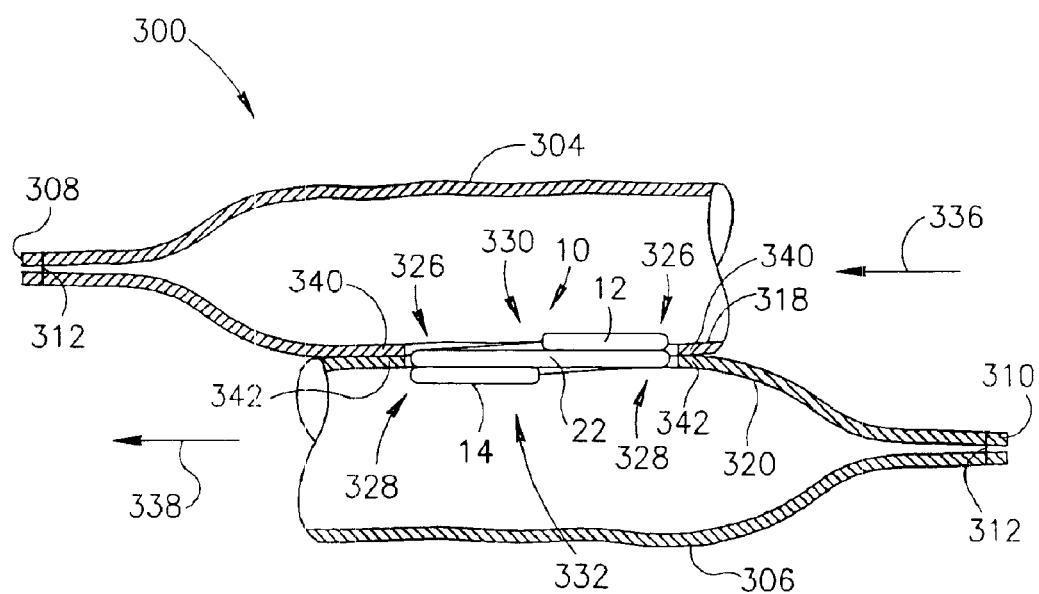

The method for performing an anastomosis procedure to join two portions of a hollow organ follows. The procedure for joining two hollow organs, such as a stomach and an intestine, is substantially similar and will be understood by persons skilled in the art. Referring now to FIGS. 22A–22D, there are seen portions referenced 304 and 306 of a hollow organ generally referenced 300, which are to be joined together by anastomosis. Hollow organ 300 includes, for example, a small or large colon, or any other hollow organ, requiring anastomosis. Alternatively, the method of the present invention is similarly employable for connection of a first hollow organ to a second hollow organ, such as the connection of a colon portion to a stomach. The method of the present invention will now be described with reference to clip 10 employed in operative attachment to a surgical clip applicator device 68, seen in FIG. 5, having a distal portion 134 described hereinabove in relation to FIGS. 8A and 8B. FIGS. 22A–22C illustrate Operational Steps for carrying out the anastomosis procedure. FIG. 22D is a cross-sectional view seen along line I—I of FIG. 22B.

Open ends referenced 308 and 310 of separated organ portions referenced respectively 304 and 306 are surgically stapled or sutured closed, referenced 312. Portions 304 and 306 of organ 300 are drawn together in an adjacent, side-by-side relationship, and adjacent walls referenced respectively 318 and 320 are perforated at punctures referenced 322 and 324, respectively, punctures 322 and 324 being adjacent. The size and shape of punctures 322 and 324 are selected, so as to facilitate positioning of loops 12 and 14 of clip 10 within respective organ portions 304 and 306 utilizing applicator device distal end 134 to which clip 10 is operatively attached.

At least the shape memory alloy portion 22 of clip 10, which is operatively attached to applicator device distal end 134, is cooled to at least its lower phase transition temperature. At this temperature, the shape memory alloy is in a martensitic state, as known in the art, intermediate portion 22 of clip 10 thus being in a plastic state. The lower phase transition temperature is generally any temperature above −273° C., although more usually it is approximately 25–35° C. below body temperature, preferably, approximately 0° C. Loops 12 and 14 are manually moved apart a predetermined distance and clip 10 is preserved in the cooled state for as long as required for insertion into organ 300.

Utilizing surgical clip applicator device distal end 134, clip 10 is introduced into organ portions 304 and 306 by inserting loops 12 and 14 via predetermined perforations 322 and 324, respectively. Loops 12 and 14 are then situated within organ portions 304 and 306, respectively, so as to straddle adjacent walls 318 and 320, respectively.

The relative positions of portions 304 and 306 of organ 300 and, applicator device 68 (FIG. 5), having distal portion 134, and clip 10 in relation thereto, must be maintained for a period of time. During this period, the temperature of organ 300 is generally effective to cause the temperature of intermediate portion 22 of the clip 10 to rise to a temperature at least equal to its upper phase transition temperature, preferably somewhat below body temperature. Thereupon, clip 10 achieves its austenitic or elastic state.

During the time that the temperature of intermediate portion 22 of clip 10 rises towards and above its transition temperature, loops 12 and 14 converge and press, respectively, against wall portions 326 and 328 of organ walls 318 and 320 respectively, located therebetween. Wall portions 326 and 328 are defined by the portions of respective walls 318 and 320 located between loops 12 and 14 of clip 10. Additionally, each of tissue portions 326 and 328 defines a wall area referenced 330 and 332, respectively, in organ walls 318 and 320, respectively. Areas 330 and 332 are substantially similar in shape and size to loops 12 and 14 of clip 10. The closing force exerted by loops 12 and 14 against portions 326 and 328 increases as the temperature of portion 22 reaches and exceeds the transitional temperature. The rate of increase in the temperature of intermediate portion 22 of clip 10 may be accelerated, for example, by warming clip 10 by any method known in the art.

Once the temperature of intermediate portion 22 of clip 10 has risen above the transition temperature, portion 22 returns fully to its elastic phase, and, as shown in FIGS. 22B, 22C and 22D, loops 12 and 14 press towards each other, against walls 318 and 320. Thus, walls 318 and 320 are maintained in a fixed position relative to each other.

Thereupon, blade 64, formed as part of a jaw element referenced 56 of distal portion 134 is manually pressed into tissue area 330 and, thereafter, area 332 by operating handles 54 (FIG. 5) against a counter element (not shown). Thus a cut aperture referenced 334 (FIG. 22B) is effected through tissue areas 330 and 332. This cut aperture 334 through tissue portions 330 and 332 creates initial patency of the gastrointestinal tract. After cut aperture 334 is effected through tissue portions 330 and 332, the only pathway from portion 304 to portion 306 of organ 300 is via cut aperture 334 in the direction indicated by arrows referenced 336 and 338 (FIG. 22D).

Furthermore, due to the pressure exerted by clip 10 on walls 318 and 320 of organ 300, respective wall areas 326 and 328 are pressed tightly against each other. Blood supply to these wall portions and to areas 330 and 332 ceases, resulting in eventual necrosis of wall areas 326, 328, 330 and 332. While areas 326, 328, 330 and 332 begin to die-off, wall tissue portions referenced 340 and 342, immediately externally adjacent thereto, begin anastomosis such that portions 340 and 342 of organ portions 304 and 306, respectively, of organ 300 become joined, and function as one continuous organ.

Once tissue portions 326, 328, 330 and 332 becomes fully necrotic, these portions together with clip 10 become separated from walls 318 and 320, resulting in an aperture (not shown) having substantially a size and shape of clip 10. Necrotic tissue portions 326, 328, 330 and 332 together with clip 10 are passed out of organ 300, via the aperture so formed, by the normal activity of the organ. For example, if organ 300 is a small intestine and the direction of peristalsis is from portion 304 towards portion 306 in the direction indicated by arrows 336 and 338, then clip 10 and necrotic tissue portions 326, 328, 330 and 332 will be passed through portion 306 in direction 338 by the normal activity of the small intestine.

After applicator device distal end 134 is withdrawn from perforations 322 and 324, these are sutured closed with one or two sutures, as closures referenced 343 and 344, respectively (FIG. 22C). With other anastomosis procedures using a stapler to join the adjacent organ walls, the requisite perforations are generally substantially larger than perforations 322 and 324 and require several staples or sutures to properly close these larger perforations.

It will be appreciated by persons skilled in the art that, instead of employing clip 10 in the surgical procedure as discussed above, and as illustrated in FIGS. 22A–22D, any of the clips seen in FIGS. 2A–3C, may be employed to effect anastomosis as is surgically appropriate. In addition, any of applicator devices 52 (FIG. 4), 68 (FIG. 5), 74 (FIG. 6), 140 (FIGS. 9A–14C), 200 (FIGS. 15A–19B), 270 (FIGS. 20A–20C) or 280 (FIGS. 21A–D), may be used to position and apply any of the clips disclosed hereinabove as is appropriate.

The method of the present invention, disclosed hereinabove in relation to FIGS. 22A–22D, includes initially surgically stapling or suturing closed 312 both organ portions 304 and 306. It will be understood by persons skilled in the art that either one or both of organ portions 304 and 306 may instead be sutured 312 closed after insertion of surgical clip 10, without departing from the scope of the invention.

Additionally, it will be appreciated by persons skilled in the art, that a device employing a shape memory alloy, such as surgical clip 10, according to embodiments of the present invention, may be described as being of one of two different types. A first type of device employs a shape memory alloy which is in an easily deformable, martensitic state when it is cooled to below room temperature, called a "Cold" type. This first device achieves a fully or partial austenitic state at room temperature, and a completely austenitic state when heated to at least its upper phase transition temperature, between room and body temperature. In a second type of device, the shape memory alloy is in an easily deformable, martensitic state at room temperature, called a "Hot" type, whereat the device is deformed and applied, and the shape memory alloy achieves a completely austenitic state when heated to above room temperature. The temperature range over which the shape memory alloy is easily deformable defines the difference between the two types of devices. Thus, utilizing a device including a shape memory alloy of the second Hot type allows more freedom in application without necessitating cooling below room temperature. The method of the present invention disclosed hereinabove relates to a device of the first Cold type, necessitating cooling below room temperature.

Considering the "Hot" type, in which the transformation temperature is higher, the clip is martensitic at room temperature and heated to about 42–45° C. to assume an austenitic state. When the temperature drops to 37° C., that is, body temperature, the martensitic transformation is not complete, leaving the clip in a transition state, with inferior mechanical characteristics.

It should be understand that the so-called transformation temperature of the alloy, in fact, is a process of transformation. Transition from a martensitic to an austenitic state starts at a temperature $A_s$ and ends with at temperature $A_f$ at which the state becomes fully austenitic. When transforming from austenitic to martensitic state, by dropping the temperature, the alloy starts to become martensitic at temperature $M_s$, and reaches a full martensitic state at temperature $M_f$.

In the Cold type, generally preferred in accordance with embodiments of the present invention, $A_f$ is lower than body temperature, generally about 25° C. In the Hot type, $M_f$ is below body temperature, so that the alloy does not become fully martensitic at body temperature.

It will, further, be appreciated by persons skilled in the art that there is a direct relationship between the size and shape of the clip used in the surgical procedure disclosed above and the size and shape of the resulting aperture in the organ. A clip of a particular size, shape and configuration is selected so as to achieve an aperture of a requisite size, shape or configuration as appropriate to the hollow organs to be subjected to anastomosis. In addition, cut 334 is indicated as effected by a blade element, as related hereinabove, formed as a straight blade. Utilizing any of the alternative blade and counter elements illustrated in the aforementioned FIGS. 7A–7H in an anastomosis clip applicator device, appropriate cut apertures are effected accordingly.

It will be appreciated by persons skilled in the art that the present invention is not limited by the drawings and description hereinabove presented. Rather, the invention is defined solely by the claims that follow.

What is claimed is:

1. A method for anastomosing a gastrointestinal tract, which includes the following steps:
  (a) gripping a surgical clip which includes:
    i) a first length of a wire having a predetermined cross-sectional shape and surface configuration, defining a closed geometrical shape having a central opening;
    ii) a second length of a wire having a predetermined cross-sectional shape and surface configuration, defining a closed geometrical shape substantially similar in configuration and magnitude to that of the first length of wire, having a central opening, wherein the first and second lengths of wire fully overlap, when configured in side-by-side registration; and
    iii) an intermediate portion located between said first length of wire and said second length of wire, said intermediate portion formed of a shape memory alloy;
  b) maintaining at least the intermediate portion of the clip at a temperature below a lower phase transition temperature thereof, whereat the intermediate portion is in a plastic state;
  c) moving the first and second lengths of wire into a position of mutual separation;
  d) drawing together portions of the gastrointestinal tract, wherein anastomosis is required, so as to bring them into an adjacent, side-by-side position, at least one of the portions being open-ended;

e) surgically sealing the open ends of the portions of the gastrointestinal tract;

f) forming predetermined perforations in adjacent walls of the adjacent portions of gastrointestinal tract and introducing the clip through the punctures, such that the adjacent portions of each wall are disposed between the first and second lengths of wire;

g) retaining the relative adjacent positions of the portions of the gastrointestinal tract and the clip in relation thereto, while raising the temperature of at least the intermediate portion of the clip to a temperature above an upper phase transition temperature, whereat the intermediate portion is in an elastic stat; thereby causing the first and second lengths of wire to attain side-by-side registration, thereby to apply a compressive force to the walls located therebetween; and h) perforating the adjacent walls, held within the central openings between the first and second lengths of wire configured in side-by-side registration for creating an initial patency of the gastrointestinal tract.

2. An anastomosis system for applying at least one surgical clip formed at least partly of a shape memory alloy, said system including, a) at least one surgical clip including:
  i) a first length of a wire, having a predetermined cross-sectional shape and surface configuration, defining a closed geometrical shape having a central opening,
  ii) a second length of a wire, having a predetermined cross-sectional shape and surface configuration, defining a closed geometrical shape substantially similar in configuration and magnitude to that of said first length of wire, wherein said first and second lengths of wire fully overlap, when disposed in side-by-side registration, and
  iii) an intermediate portion located between said first length of wire and said second length of wire, said intermediate portion formed of a shape memory alloy;
wherein, when at a first temperature or higher, said first and second lengths of wire are positioned in a side-by-side closed position and said shape memory alloy is in an elastic state, and further, when at a second temperature or lower, below said first temperature, said shape memory alloy is in a plastic state, thereby enabling said first and second lengths of wire to be moved into and to retain a spaced apart position, and upon heating of said clip to a temperature at least equal to said first temperature, said first and second lengths of wire return to said side-by-side closed position, thereby to apply a compressive force to tissue located therebetween; and b) an anastomosis clip applicator device for applying the surgical clip to press together adjacent wall portions of adjacent hollow organ portions so as to effect anastomosis between the adjacent organ portions, wherein said applicator device includes:
  i) gripping apparatus for gripping the surgical clip, configured to permit positioning of the clip into a pair of adjacent hollow organ portions;
  ii) a release mechanism, associated with said gripping apparatus, for selectably releasing said clip from said gripping apparatus when the clip is positioned in a selected position about a pair of organ walls to be anastomosed;
  iii) tissue cutting apparatus having a predetermined configuration, operatively associated with said gripping apparatus, selectably operable, after positioning of the clip, to cut through the tissue walls so as to form therethrough a predetermined perforation; and
  iv) apparatus for activating said gripping apparatus, said release mechanism and said cutting apparatus, so as to introduce and apply the surgical clip into adjacent hollow organ portions, such that the surgical clip compresses together the adjacent walls of the hollow organ portions, and thereafter causes said cutting apparatus to perforate the adjacent pressed together organ walls.

3. The system according to claim 2 wherein said cutting apparatus includes:
  a) a blade element having a predetermined configuration; and
  b) a counter element having a predetermined configuration, wherein said blade and counter elements are arranged in mutually opposing registration, and adapted to be closable in mutual mating engagement, thereby to perforate tissue located therebetween.

4. The system according to claim 2, wherein said geometrical shape is substantially a shape selected from the group including: circular; and elliptical.

5. The system according to claim 2, wherein said first length of wire and said second length of wire are defined by a continuous coil.

6. The surgical clip according to claim 2, wherein said first length of wire and said second length of wire are two distinct lengths of wire, each defining a closed geometrical shape.

7. The system according to claim 2, wherein at least one of said first length of wire and said second length of wire is formed having a cross-sectional shape substantially as selected from the group including:
  a) circular;
  b) circular, having planar surfaces formed therein such that, when configured in side-by-side registration, said planar surfaces of said first and second lengths of wire fully overlap thereby to control pressure applied to tissue compressed therebetween; and
  c) elliptical, thereby to control pressure applied to tissue compressed between said first and second lengths of wire.

8. The system according to claim 2, at least one overlapping surface of at least one of said first length of wire and said second length of wire is formed having a surface configuration selected from at least one of the group including:
  a) a plurality of parallel surface grooves;
  b) knurled;
  c) a plurality of spikes; and
  d) a plurality of studs.

9. The system according to claim 2, wherein said gripping apparatus includes at least one pair of fastener elements for securing said clip to said applicator device.

10. The system according to claim 2, wherein said counter element is a second blade clement.

11. The system according to claim 2, wherein said applicator device includes ejector apparatus for disengaging and ejecting the clip from said gripping apparatus.

12. The system according to claim 2, wherein said applicator device has a proximal end portion and a distal end portion and wherein said gripping apparatus, said blade element and said at least one counter element are formed at said distal end.

13. The system according to claim 12, wherein said distal end portion is detachable from said proximal end portion.

* * * * *